United States Patent [19]

Nolan et al.

[11] Patent Number: 5,404,877
[45] Date of Patent: Apr. 11, 1995

[54] LEADLESS IMPLANTABLE SENSOR ASSEMBLY AND A CARDIAC EMERGENCY WARNING ALARM

[75] Inventors: James A. Nolan, Conifer; Bruce M. Steinhaus, Parker; Tibor A. Nappholz, Englewood, all of Colo.

[73] Assignee: Telectronics Pacing Systems, Inc., Englewood, Colo.

[21] Appl. No.: 72,570

[22] Filed: Jun. 4, 1993

[51] Int. Cl.$^6$ ............................. A61B 5/0205
[52] U.S. Cl. .................. 128/671; 128/695 R; 128/734; 607/63; 607/20; 607/2; 607/6
[58] Field of Search ............ 607/27, 32, 65, 60, 607/63, 2, 6, 18, 19, 20; 128/671, 702, 705, 695, 734

[56] References Cited

U.S. PATENT DOCUMENTS

| | | | |
|---|---|---|---|
| 4,223,679 | 9/1980 | Schulman et al. | 607/32 |
| 4,295,474 | 10/1981 | Fischell | 128/697 |
| 4,625,730 | 12/1986 | Fountain et al. | 607/27 |
| 4,692,719 | 9/1987 | Whigham | 332/11 |
| 4,702,253 | 10/1987 | Nappholz et al. | 128/419 PG |
| 4,825,869 | 5/1989 | Sasmor et al. | 607/27 |
| 4,886,064 | 12/1989 | Strandberg | 607/18 |
| 4,901,725 | 2/1990 | Nappholz et al. | 128/419 PG |
| 5,003,976 | 4/1991 | Alt | 607/18 |
| 5,042,497 | 8/1991 | Shapland | 128/702 |
| 5,058,583 | 10/1991 | Geddes et al. | 607/18 |
| 5,076,272 | 12/1991 | Ferek-Petric | 607/28 |
| 5,088,491 | 2/1992 | Schaldach | 607/18 |
| 5,113,869 | 5/1992 | Nappholz et al. | 128/696 |
| 5,197,467 | 3/1993 | Steinhaus et al. | 128/419 PG |
| 5,201,808 | 4/1993 | Steinhaus et al. | 128/419 PG |

*Primary Examiner*—William E. Kamm
*Assistant Examiner*—Kennedy J. Schaetzle
*Attorney, Agent, or Firm*—Gottlieb, Rackman & Reisman

[57] ABSTRACT

A leadless implantable cardiac arrhythmia alarm is disclosed which continuously assesses a patient's heart function to discriminate between normal and abnormal heart functioning and, upon detecting an abnormal condition, generates a patient-warning signal. The alarm is capable of sensing impedance measurements of heart, respiratory and patient motion and, from these measurements, generating an alarm signal when the measurements indicate the occurrence of a cardiac arrhythmia. Because it requires no external leads or feedthrough connectors, the hermetically-sealed patient alarm is minimally invasive and results in reduced trauma to a patient.

44 Claims, 11 Drawing Sheets

LEADLESS IMPLANTABLE SENSOR ASSEMBLY AND A CARDIAC EMERGENCY WARNING ALARM

TECHNICAL FIELD

The present invention relates to a chronically implantable cardiac emergency warning alarm, and to a method of operating such an alarm. More particularly, it relates to an alarm and a method for continuously assessing a patient's heart function to discriminate between normal and abnormal heart functioning and, upon detecting an abnormal condition, for generating a patient-warning signal.

BACKGROUND OF THE INVENTION

Ventricular arrhythmias are potentially lethal. In the instance of chaotic, non-coordinated cardiac contraction, known as fibrillation, death may occur within minutes. For patients who have survived an episode of ventricular fibrillation, there is a high probability of recurrence. In addition, patients who have experienced sustained symptomatic ventricular tachycardia are at risk in that such arrhythmias may convert to fibrillation. It is these patients who may benefit from an implantable cardioverter or defibrillator.

Many patients are afflicted with cardiac disease such that a potentially lethal ventricular arrhythmia is possible, but not sufficiently likely to warrant the trauma, inconvenience and costs associated with an implanted anti-arrhythmia device. These patients may be better served by an alarm device which warns of the occurrence of an arrhythmia but does not apply therapy to the heart. Thus, when the alarm detects an arrhythmia condition and emits a warning signal, the patient may seek medical assistance.

Such an alarm device may also benefit patients having an implanted cardioverter or defibrillator. In these patients, an implantable cardiac condition alarm provides an early warning alarm signal so that the patient may take precautionary steps to reduce the threat associated with sudden incapacity due to an arrhythmia condition. For example, when ventricular fibrillation occurs, a patient commonly reaches an unconscious state within five to fifteen seconds following the onset of fibrillation due to lack of oxygen to the brain. If such a patient experiences ventricular fibrillation while performing an activity, such as standing or driving an automobile, a warning signal may allow the patient to take an appropriate action to avoid the consequences of becoming suddenly unconscious. Thus, a patient is alerted to the onset of a cardiac abnormality to terminate a risky activity or to obtain medical attention when it becomes practical.

U.S. Pat. No. 4,295,474, entitled "Recorder with Patient Alarm and Service Request Systems Suitable for use with Automatic Implantable Defibrillator", issued Oct. 20, 1981, to R. E. Fischell, discloses a system and apparatus, particularly adapted for use with an automatic implanted defibrillator, that monitors electrocardiogram data signals to provide a continuously updated recording of the ECG data. The recorder responds to the operating conditions of the automatic implanted defibrillator device and places into electronic storage, for subsequent readout to the patient's doctor, ECG data both immediately preceding the onset of ventricular fibrillation and also during the subsequent defibrillation activity, when one or more high energy electrical impulses are applied to the patient's heart. In addition, this recorder operates to automatically alert the patient when ventricular fibrillation has been detected and defibrillation is to be attempted, so that appropriate precautions may be taken. Moreover, following defibrillation, the patient is alerted in a distinctive manner that defibrillation has occurred and that a physician should be contacted.

The Fischell monitoring device requires electrode leads for sensing ECG signals. In an implanted device, the leads are generally extended through the patient's body, through the circulatory system to make a direct electrical connection with the heart. Some trauma to the patient is involved in implanting the leads. Further disadvantages of the leads are that they are subject to breakage and the point of connection between the leads and the monitor may allow leakage of biological fluids into the monitor.

U.S. Pat. No. 5,113,869, entitled "Implantable Ambulatory Electrocardiogram Monitor", which issued to T. A. Nappholz et al. on May 19, 1992 describes an implanted programmable ambulatory electrocardiography (AECG) patient monitoring device that chronically senses and analyzes electrocardiographic signals from at least one subcutaneous precordial sensor to detect electrocardiogram and physiological signal characteristics predictive of cardiac arrhythmias. The device includes telemetric capabilities to communicate a warning signal to an external device when such arrhythmias are predicted.

The Nappholz et al. AECG monitoring device is attached to one or more leads for sensing cardiac electrical signals, which may be introduced subcutaneously into the patient's tissue using a tunneling device or a very fine blunt needle. Unfortunately, the implantation of the leads into the patient's tissue is a surgical procedure which does involve some trauma to the patient. Furthermore, movement by the patient can cause stresses upon the implanted lead, possibly resulting in dislodging or breaking of the lead, as well as irritation of the patient's tissue. Furthermore, the lead does pose some risk of infection to the patient.

The present invention provides an implantable alarm that is hermetically sealed and leadless. Because there are no leads, implantation of the alarm is minimally invasive. Furthermore, the absence of leads allows hermetic sealing of the alarm to avoid the risk of biological fluid leakage into the alarm which could render the device inoperable or cause faulty operation.

Because the alarm is implantable, its acquired physiological signals have good fidelity and consistency over time. For an alarm to chronically and constantly monitor a patient's heart condition and trigger a warning signal when medical intervention is necessary, it must be continuously reliable. Prior art monitoring devices are not sufficiently reliable for long-term monitoring. For example, electrocardiogram analysis performed using existing external or body surface AECG systems is limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration. Signal degradation in prior art AECG monitors also occurs due to contact problems, ECG waveform artifacts, and patient discomfort. Externally attached electrodes are subject to motion artifacts from positional changes and the relative displacement between the skin and the electrodes. External electrodes are impractical for long-term monitoring (longer than 24 hours).

Furthermore, external electrodes require special skin preparation and care by the patient to prevent signal corruption by dislodgement or wetting from sweating or bathing. Externally attached electrodes lack the signal fidelity required to automatically perform data analysis for automatically identifying dangerous arrhythmia conditions. Externally attached electrodes cannot chronically produce the cardiac data necessary for a reliable patient alarm. In prior art AECG recordings, physicians could pick and choose the best cardiac waveforms for visual and semi-automated analysis. A continuously responsive and chronically implanted warning device cannot select its signals for analysis. All signals must permit reliable analysis.

The implantable character of the alarm of the present invention changes the nature of a cardiac monitoring device in three ways. First, long-term and constant monitoring is practical only in an implantable system. Secondly, the absence of surface electrodes substantially increases system accuracy. Lastly, information is not altered by modification of a patient's behavior.

The present invention provides a hermetically sealed and leadless implantable alarm employing a sensor capable of measuring multiple physiological parameters. This sensor provides measurements of heart motion, respiration and patient motion. The alarm analyzes the heart motion parameter to determine a patient's heart rate. Other sensed physiological parameters may be determined by the alarm and used to derive an indication of the patient's metabolic demand. This metabolic demand indication may be further used to determine heart rate thresholds which indicate whether the patient's heart rate is normal or abnormal. Thus, an elevated heart rate will trigger the alarm when the patient is at rest but, appropriately, the same rate does not activate the alarm for an exercising patient. The alarm actives a warning signal when the heart rate is abnormal.

The sensor for the alarm of the present invention measures and analyzes impedance signals that relate to changes in impedance within the volume of tissue penetrated by the electromagnetic field generated by the sensor. These changes may be related to physiological function. The alarm determines a heart motion parameter over time, orders these parameters into a heart motion signal sequence and then analyzes this sequence to determine the patient's heart rate. The alarm may perform further analysis of the heart motion signal to determine other physiological parameters, such as stroke volume or cardiac output. For example, the alarm may process the heart motion signal to determine right ventricular stroke volume and set the patient's metabolic demand accordingly.

In one embodiment, the alarm of the present invention measures heart rate and may be programmed to activate a warning signal either when the measured heart rate exceeds a programmed maximum rate or when the measured heart rate exceeds an automatically-determined threshold heart rate derived from a physiological sensor measurement. The heart rate and physiological measurement are both acquired using the same sensor hardware.

In this manner, the present invention provides a physiological sensor, hermetically sealed within an implantable cardiac function alarm, which allows the alarm to compare the patient's heart rate to metabolic demand, determine whether the heart rate is appropriate with respect to the metabolic demand and generate a warning signal when the heart rate is inappropriate. The operation of the sensor may be altered by means of programming of the alarm from an external communicating device. These alterations in sensor operation fulfill the needs of various patients who are afflicted with different cardiac and respiratory health problems. Importantly, this sensor does not require a lead. Thus, the alarm may implanted with little trauma to the patient.

In addition to measuring heart motion, the sensor may be programmed or controlled to measure physical activity, also called patient motion, to provide an estimate of metabolic demand. One advantage of a patient motion sensor is its very rapid response time to the onset of exercise. Therefore, the patient motion sensor can track rapid increases in heart rate that would trigger a false arrhythmia alarm if a slower sensor were used to determine a patient's metabolic demand. A patient-motion sensor responds favorably to patient activities which create vibration, such as jogging, walking and stair climbing. Unfortunately, activities such as bicycling do not promote metabolic demand analysis because little vibration occurs. A disadvantage of a physical activity sensor is that it is not generally regarded as a truly physiologic sensor because it does not measure true metabolic demand and, therefore, is not affected by emotional stimuli or pyrexia. Although the lack of a truly physiological response is generally considered a disadvantage of a motion sensor, the fact that this sensor acts independently from physiologic variables may provide a better response under conditions in which patient systems or tissues are diseased. For example, a motion sensor may supply a better signal for responding to exercise than a respiration sensor will under conditions of lung disease, such as emphysema. A further disadvantage of a patient motion sensor is the difficulty of attaining a scaled response to gradations of metabolic demand. Patient motion sensors generally act in an on/off fashion, in which a sensor is unable to detect changes in patient workload. Therefore, the sensor response does not normally depend on the amount of exercise the patient is performing, but instead the measurement remains identical so long as the measured activity is above a preprogrammed level.

The sensor also may measure and analyze impedance signals which relate to a patient's respiratory function to determine metabolic demand. The respiratory parameter which correlates most closely to a patient's metabolic demand and appropriate heart rate is minute ventilation, a highly physiologic variable which reflects closely the metabolic demands of exercise. The body's increase in minute ventilation during exercise parallels its oxygen uptake but also reflects changes in cardiac output and heart rate. Minute ventilation not only correlates well with exercise, but also varies in response to stress and pyrexia. U.S. Pat. No. 4,702,253 (hereinafter called the "'253 patent"), entitled "Metabolic-Demand Pacemaker and Method of Using the Same to Determine Minute Volume" issued to T. A. Nappholz et al. on Oct. 27, 1987, discloses a rate-responsive pacemaker which senses impedance in the pleural cavity of a patient and derives respiratory minute volume from impedance. The pacemaker then employs the respiratory minute volume, a measure of the amount of air inspired by a person as a function of time, as a rate-control parameter. The greater the amount of air inspired, the greater the need for a higher pacing rate. The device described in this patent requires a nonstandard pacing lead in order to perform the minute volume measurement.

U.S. Pat. No. 4,901,725 (hereinafter called the "'725 patent"), entitled "Minute Volume Rate-Responsive Pacemaker", issued to T. A. Nappholz et al. on Feb. 20, 1990, discloses a pacemaker which performs a rate-responsive function in the manner of the '253 patent with various improvements, and, in addition, only requires standard pacing leads. To measure the intravascular impedance, the minute-volume sensor generates a low energy current pulse at 50 ms intervals between a ring electrode of the lead and the pulse generator case, then measures the voltage between the tip electrode of the lead and the pulse generator case arising from the applied current. An intravascular impedance value is determined from the measured voltage and the applied current using Ohm's law. Transthoracic impedance increases with inspiration and decreases with expiration, and its amplitude varies with the tidal volume. The impedance signal thus comprises two components, representing tidal volume and respiratory rate. Pulse generator circuitry identifies the two signals and processes them to yield minute ventilation. The minute-volume-controlled rate-responsive pacemaker employs a highly physiologic sensor. Its ability to assess the metabolic demands of the body is superior to that of a pacemaker driven by respiratory rate alone, since depth of ventilation is an important response to exercise or stress. The apparatus described in the '725 patent requires no more than standard pacing leads, although the leads cannot be unipolar leads, and programming of minute ventilation rate adaptation necessitates only a single exercise test.

Impedance sensors are also disclosed by B. M. Steinhaus et al. in U.S. Pat. No. 5,197,467, entitled "Multiple Parameter Rate-Responsive Cardiac Stimulation Apparatus", which issued Mar. 30, 1993, and in U.S. Pat. No. 5,201,808, entitled "Minute Volume Rate-Responsive Pacemaker Employing Impedance Sensing on a Unipolar Lead", which issued Apr. 13, 1993. These two patents are assigned to the assignee of the present application.

SUMMARY OF THE INVENTION

Briefly stated, and in accordance with a first embodiment of the present invention, there is provided a leadless cardiac arrhythmia alarm for chronic implantation within a patient's body, including a hermetically-sealed housing and, enclosed within the housing, a subcutaneous electromagnetic sensor for sensing physiological signals, a cardiac arrhythmia detector for analyzing the sensed physiological signals to determine when such signals are abnormal, and an acoustic or audio alarm for triggering a warning signal when the physiological signals are abnormal. The sensor may be controlled or programmed to measure one or more parameters indicative of physiological signals. The sensor includes an antenna, means for applying at least one characteristic signal waveform of measuring currents to the antenna, and means for measuring voltages from the antenna in response to the application of the measuring currents. The sensor further includes means for controlling the frequency applying means to limit the frequency components of the applied measuring currents to lie within at least one predetermined subrange of frequencies such that the measured voltage within each subrange of frequencies corresponds to a measurement of physical motion within the patient's body relating to a particular physiological function. Additionally, the sensor includes means for deriving at least one physiological parameter from the measured voltage corresponding to each of the at least one predetermined subrange of frequencies. The applied measuring currents are constrained to have frequency components within a range of from approximately 10 kilohertz to approximately 1000 megahertz.

The frequency controlling means within the sensor provides for generation of measuring current in the form of either: (1) short-duration, square-wave-like current pulses, (2) sinusoidal-like oscillating current or (3) short-duration pulses of sinusoidal-like oscillating current. Current pulses range in duration from 5 ns to 20μs. Oscillating current ranges in frequency from 10 kHz to 1000 MHz, and may be generated continuously or in pulses as short as 5 ns. The frequency controlling means sets the frequency of the measuring current for the purpose of measuring one or more particular metabolic-demand parameters. If the measuring currents are in the form of short-duration, square-wave-like current pulses or short-duration pulses of sinusoidal-like oscillating current, the frequency controlling means sets the pulse duration. If the measuring currents are in the form of sinusoidal-like oscillating current, the frequency controlling means sets the oscillation frequency.

One possible metabolic-demand parameter is based on heart motion. Its associated subrange of pulse durations is approximately 300 nanoseconds or larger. Its associated subrange of oscillation frequencies is approximately 4 Mhz or lower. The cardiac arrhythmia detector derives a heart rate measurement on the basis of the heart motion physiological parameter and detects a physiological condition indicative of a heart abnormality when the heart rate parameter is greater that a predetermined abnormal heart rate. A second possible metabolic-demand parameter is based on respiration. Its associated subrange of durations includes pulses from approximately 50 nanoseconds to approximately 400 nanoseconds. Its associated subrange of oscillation frequencies extends from approximately 1 megahertz to approximately 11 megahertz. The cardiac arrhythmia detector may derive a metabolic indicator rate on the basis of the respiration parameter and set the predetermined abnormal heart rate as a function of the metabolic indicator rate. A third possible metabolic-demand parameter is based on patient motion. Its associated subrange of durations is approximately 125 ns or shorter. Its associated subrange of oscillation frequencies is approximately 8 Mhz or higher. The cardiac arrhythmia detector may derive a metabolic indicator rate on the basis of the respiration parameter and set the predetermined abnormal heart rate as a function of the metabolic indicator rate.

In accordance with a second embodiment of the present invention, there is provided a leadless cardiac arrhythmia alarm, which is similar to the aforementioned first embodiment of the alarm except that, instead of including an acoustic alarm to generate a warning signal for the patient, there is included a transmitter for communicating a warning signal to a non-implanted information-receiving device. This second embodiment of the alarm operates continuously, independently of signals that may be generated by the information-receiving device.

Furthermore, the sensor is capable of performing measurements characteristic of activity or motion that are additional to the measurement of vibration alone. At high interrogating frequencies, the sensor measures motion of the housing of the implantable device relative to the surrounding tissue. At lower interrogating frequencies, the sensor measures more of a total body impedance than local impedance changes alone so that it can measure leg or lower torso motion. In this case, interrogating frequencies must approximately equal one of the many resonant frequencies of the body. Thus a true indicator of physical activity can be measured, rather than merely the detection of vibration.

This embodiment of the alarm attempts to initiate communication independently of signals that may be generated by the information-receiving device.

In accordance with a third embodiment of the present invention, there is provided a method for monitoring a patient's heartbeat signals using a hermetically-sealed cardiac arrhythmia alarm apparatus to detect and warn of a cardiac arrhythmia condition. This method includes a first step of measuring impedance within the patient's body. The impedance measuring step consists of the substeps of applying at least one characteristic signal waveform of measuring current to an antenna and measuring voltages from the antenna in response to the application of the measuring current. This antenna is fully enclosed within the apparatus. The measuring current applying step applies current having frequency components within a range from approximately 10 kilohertz to approximately 1000 megahertz. The method further includes the step of controlling the measuring frequency components of the applied measuring current to lie within at least one predetermined subrange of frequencies such that the measured voltage within each subrange of frequencies corresponds to a measurement of a physiological parameter. Next the method comprises the steps of deriving at least one physiological parameter from the measured voltage corresponding to each of the predetermined subranges of frequencies and analyzing the derived physiological parameters to detect a physiological condition indicative of a heart abnormality. Upon detecting a heart abnormality, the method includes the steps of initiating communication with a non-implanted message-receiving device independent of the operation of the message-receiving device and transmitting diagnostic messages to the message-receiving device upon initiation of communication.

BRIEF DESCRIPTION OF THE DRAWINGS

Further objects, features and advantages of the invention will become apparent upon consideration of the following detailed description in conjunction with the accompanying drawings, in which.

DETAILED DESCRIPTION

Figure 1:
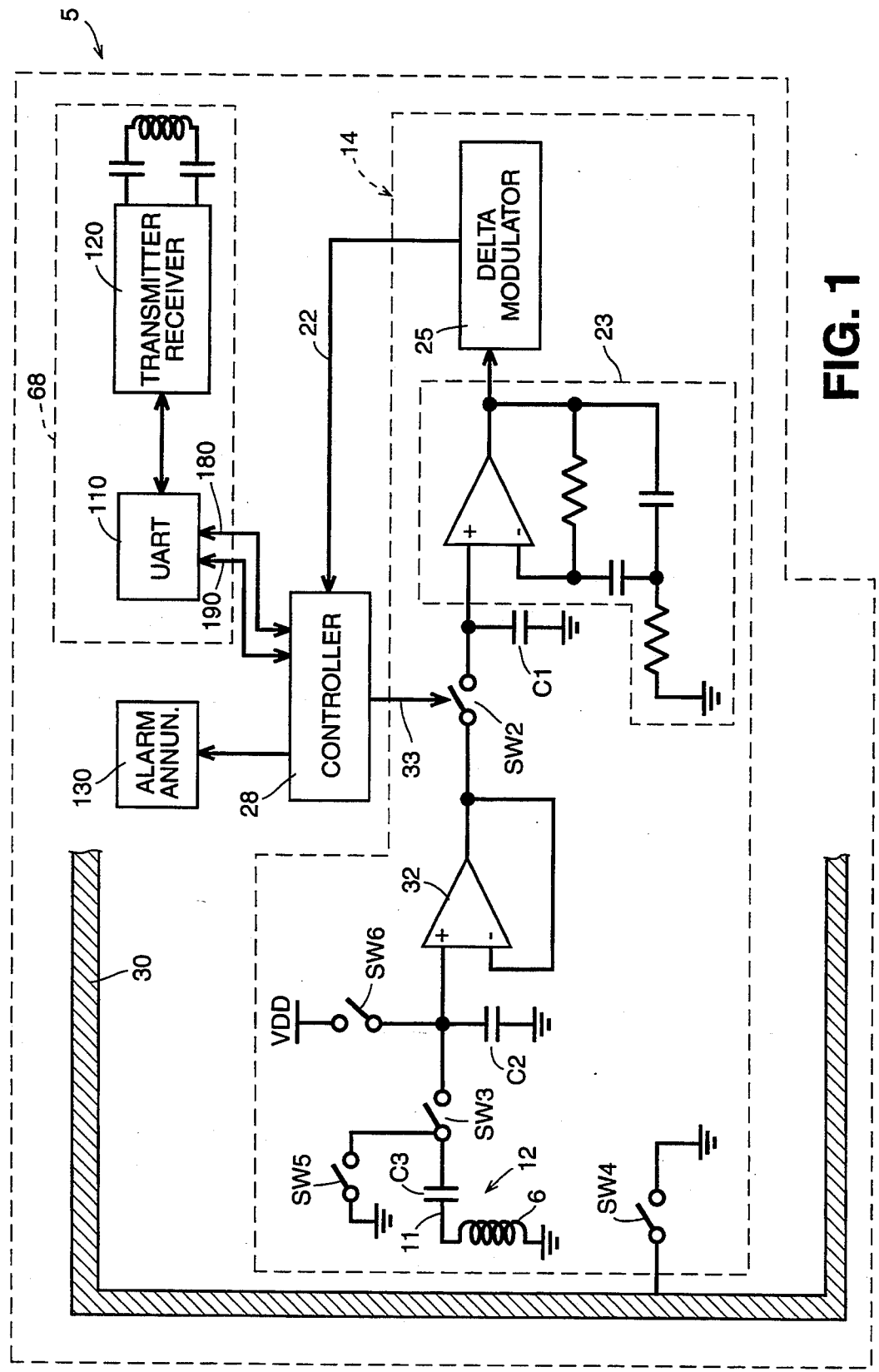
FIG. 1 is a schematic circuit diagram of an implantable cardiac arrhythmia alarm in accordance with one embodiment of this invention.

The drawing of FIG. 1 is a schematic circuit diagram of the apparatus of the invention in the form of a physiological signal monitor and alarm, shown generally at 5, that includes a housing 30. All alarm logic is under the control of a controller 28 (which may include a microprocessor). The controller 28 controls the telemetry receiver/transmitter function, memory reading and writing, acquisition of sensed signals, and real-time clock functions to provide the capability of shutting down the entire system when idle. The controller provides standard functionality including timers and an input/output (i/o) port, neither of which is individually shown. The controller 28 opens and closes various switches in the alarm 5. The controller 28 reads from and writes to a universal synchronous receiver/transmitter (UART) 110 via a control/address bus 180 and a data bus 190, and writes to an impedance measurement circuit 14 on output line 33, in controlling operations of the alarm 5.

Figure 12:
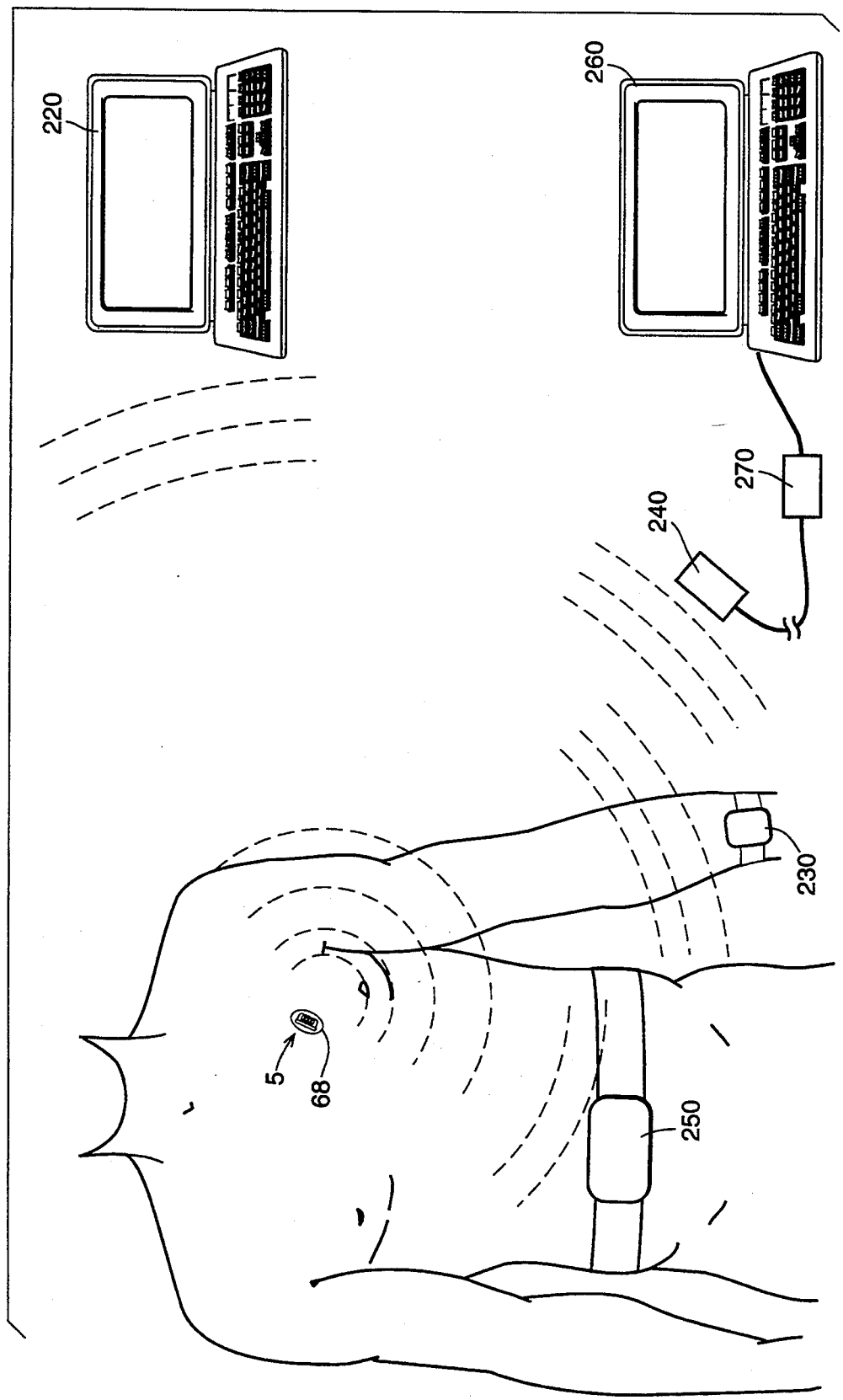
FIG. 12 is an illustration of the telemetric interconnections between the cardiac arrhythmia alarm and various external devices.

A telemetry receiver/transmitter 68 performs two-way, digital telemetry to transfer data and programs between the implantable alarm 5 and an external device, for example an external programmer and analyzer 220 (FIG. 12). While performing normal operations, the alarm 5 may receive from the external programer and analyzer a downloaded program object code and other control information to govern data acquisition by the alarm 5. Under the direction of commands from the external programmer and analyzer, the alarm 5 may reply with acquired and processed physiological data. It also is a normal operation for the alarm 5 to acquire and process the physiological data and from this data analysis to detect warning conditions.

The alarm 5 is provided with an alarm annunciator (FIG. 1) which, via control signals from the controller may emit an acoustic alarm signal to notify the patient of an arrhythmia event by hearing a sound or feeling a vibration. In this mode of operation, determined by and under the direction of the downloaded program code, the alarm may initiate communication with an external device, for example an external programmer and analyzer 260 (FIG. 12) in a health care provider's office, to warn of abnormal physiological conditions. (The alarm 5 may also warn the external device of a malfunction in response to an attempt and failure of a self-diagnostic test.)

The telemetry receiver/transmitter 68 is made up of an rf transmitter/receiver unit 120 and the UART 110, which directs data flow from the rf circuits to the data bus under the control of the controller 28. The alarm 5 transmits information to an external device within a range of at least about 20 feet, at a telemetric data transmission frequency of 40 to 200 MHz. The rf receiver of unit 120 modulates the telemetric frequency at a frequency that is in the order of about 2 MHz. The UART 110 controls data communications in response to input-/output commands from controller 28, which configure the UART 110 to perform reception or transmission. UART 110 includes a standard serial interface, a data buffer, and circuitry for error detection coding and decoding. None of these circuit elements are individually shown, but they are standard in the art of computer communications.

When the telemetry receiver/transmitter 68 is idle, the controller 28 disconnects power to the communication circuitry. In one intended mode of operation the controller may detect a predetermined physiological or operational condition, while analyzing data or performing self-diagnostics, which will trigger communication with a nearby external device. Upon detecting this condition, the controller will transmit a beacon signal to the external device. The beacon signal informs the device that the alarm 5 will change its communication mode from transmission to reception and listen for control information for a short time window following the beacon. For example, an idling microprocessor may send beacon signals every five seconds to allow communication to begin within a 2 millisecond window.

All switches shown in FIG. 1 are directly or indirectly under the control of the controller 28. One output line 33 of the controller 28 is shown extending to switch SW2, but it is to be understood that the switches SW3, SW4, SW5 and SW6 are similarly controlled. The alarm 5 makes an impedance measurement when the controller 28 controls output line 33 to activate the impedance measurement circuit 14.

The impedance measurement circuit 14 shown in FIG. 1 operates in a pulsed mode. The impedance measurement circuit 14 includes a connection through a switch SW4 to the alarm housing 30, and a connection through a switch SW3 to an antenna line 11 and an inductor or coil 6. The impedance measurement circuit 14 employs an antenna system 12, comprising the antenna line 11 and antenna coil 6, for applying a source measuring current to the patient's body, and measures the impedance to the flow of current between the antenna system 12 and the patient's body. A buffer 32 and a filter 23 are also employed in circuit 14. The impedance measurement circuit 14 senses impedance by sending current pulses to and measuring the resulting voltages on the antenna system 12. The proximal end of antenna coil 6 is electrically connected via line 11 to a coupling capacitor C3. Switch SW5, which is held open during an impedance measurement operation, may be closed for other operations to discharge the coupling capacitor C3. The distal end of the coil 6 may be connected to reference ground within the alarm 5. Alternatively, the distal end of the coil 6 may connect to other points within the housing 30.

Figure 4:
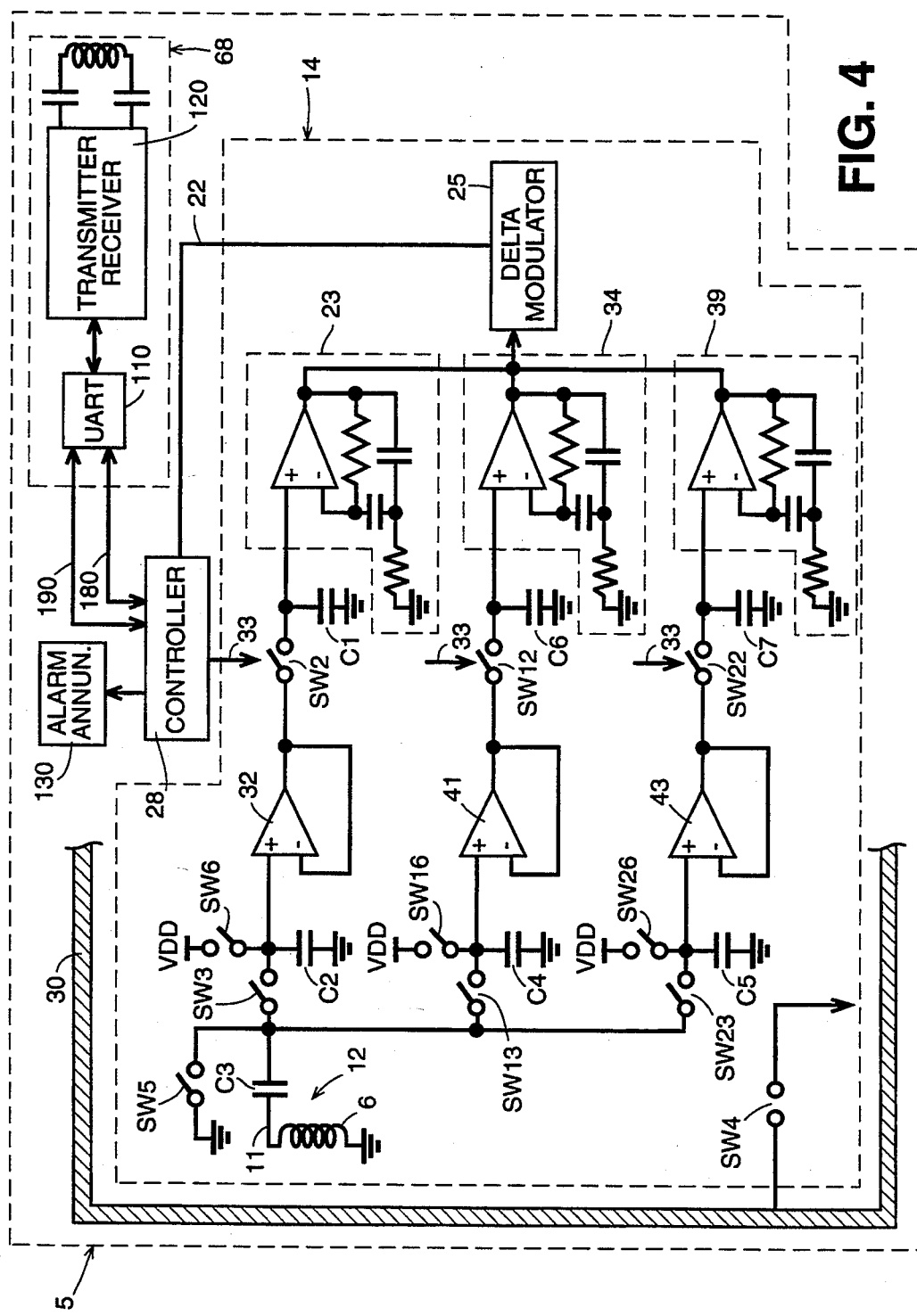
FIG. 4 is a schematic circuit diagram of an implantable cardiac arrhythmia alarm in accordance with a second embodiment of this invention, which incorporates an impedance measurement circuit having three individual signal processing paths for processing different types of physiological information.

Although the embodiments of the invention shown in FIGS. 1 and 4 implicitly depict the housing 30 to be a metallic container that is coupled to reference ground by the switch SW4, other embodiments intended to be within the scope of the invention include alarms in which the housing 30 is not a metallic container, but rather may be in the form of a ceramic case, an epoxy case or a case that combines metallic, ceramic and epoxy materials. For example, a case may be constructed of metal, ceramic or epoxy materials and include a ceramic window in the vicinity of the coil 6 and/or the antenna of the transmitter/receiver 120 to provide for unobstructed transmission of electromagnetic signals to the body and to an external programmer.

The inductance of coil 6, which is the primary component of antenna system 12, may range from 10 nH to 1 mH, and is selected to provide a high degree of electrical coupling to the tissue. For example, if the inductance is too small, the electrical field energy generated by the coil 6 will be too small to detect changes in impedance which relate to physiological phenomena. Also, the magnitude of the inductance may be varied according to the range of frequencies to be transmitted into the tissue. For example, an inductance of 10 nH may be employed when a measuring frequency of about 330 MHz is applied to the tissue, and an inductance of 1 mH may be used for a measuring frequency of approximately 500 kHz.

The impedance measurement circuit 14 measures the input impedance of the coil 6 or antenna 11. The coil/antenna functions by generating an electromagnetic field external to alarm 5. The input impedance of the coil/antenna depends both on the size of the coil/antenna and the properties of the medium permeated by the field. If the electromagnetic field impinges on organs that move or change in size, then this motion or dimensional variability will cause the input impedance of the coil/antenna to change.

The characteristics of the interrogated field may be relevant in determining the physical size of inductor or coil 6. A larger sized inductor may be used to interrogate a specific area, such as a heart valve, a particular blood vessel or a heart chamber. A smaller sized inductor may be used to measure impedance in a more general area or for measuring multiple parameters. Furthermore, the inductor may be selected such that its physical size matches the dimensions of the organ or structure to be interrogated.

The coil 6 can be resonated by appropriate selection of the interrogating frequency and the inductive and capacitive reactance of the circuit to increase the circulating current, thereby enlarging the measured field and raising the sensitivity of the measurement. The electromagnetic field produced by the impedance measurement circuit 14 is controlled in both magnitude and direction by the geometry of the coil/antenna and the frequency of the applied electromagnetic field. Very small coils 6 can apply a field to a very specific anatomic area. Larger coils 6 apply a more global field. The coil/antenna can be made to apply a field more specifically by employing a reflector or screen (neither of which is shown) for example in the form of a dish or annular rings, inside the housing 30 to prohibit the electromagnetic field from extending into certain regions. When the coil/antenna length exceeds a significant percentage of the wavelength of the sensing frequency, then the field pattern of the coil/antenna is determined by the sensing frequency rather than the coil/antenna size.

Considering the operation of the impedance measurement circuit 14 during a single impedance measurement cycle, the controller closes switch SW6 to charge a measuring capacitor C2 to a regulated voltage source VDD. Subsequently, the controller opens switch SW6 and closes switches SW3 and SW4, while holding switches SW2 and SW5 open, for a predetermined measuring interval $\Delta T$, thereby connecting capacitor C2 to antenna system 12 through coupling capacitor C3. While the switches SW3 and SW4 are closed, measuring capacitor C2 discharges through capacitor C3 into the antenna system 12, causing current to flow through the antenna system and thereby decreasing the voltage across measuring capacitor C2. The amount by which the voltage across the measuring capacitor C2 diminishes depends on the impedance of the surrounding tissue. The impedance of the surrounding tissue is the object of the measurement.

The measuring current which is applied to the antenna system 12 has frequency characteristics in the range of from about 10 kHz to about 1000 MHz, depending on the duration of the measuring interval $\Delta T$. At these measuring current frequencies, the antenna system creates a displacement current in the body. This displacement current is fundamentally different from the conduction current which is generated by prior art impedance-measuring monitors such as those shown in the aforementioned '253 and '725 patents. As an alternative to generating a measuring current in the form of pulses, as in the embodiment shown in FIG. 1, an alternate form of the impedance measurement circuit 14 may generate a measuring current in the form of sinusoidal-like oscillating current, short-duration pulses of square-wave-like current, or timed pulses of sinusoidal-like oscillating current.

The impedance measurement circuit 14 measures spatial impedance by determining the potential upon the antenna system 12, which is essentially embodied in the coil 6. In the preferred embodiment of the alarm 5, the impedance measurement circuit 14 derives samples at a rate of about 20 per second and communicates these samples to controller 28 via a conductor 22.

Although the impedance measurement circuit 14 of FIG. 1 measures impedance changes by applying a voltage to the antenna 11 and measuring the resulting current, the scope of the present invention extends to other embodiments that measure impedance in a different manner. For example, some embodiments of the invention apply a current to the antenna 11 and measure the resulting voltage. Other embodiments apply a voltage through a voltage divider (not shown), and measure the resulting voltage at a different port of the divider. In some additional embodiments, an oscillator (not shown) is coupled to the antenna 11 across a load and the impedance measurement circuit is measured across the load. In a further exemplary embodiment of the invention, a capacitor (not shown) or inductor (not shown) is discharged to apply an interrogating pulse of steady voltage or current and the current or voltage resulting from the interrogating pulse is measured at a specified time.

Resuming consideration of the operation of the impedance measurement circuit 14 during a single impedance measurement cycle, measuring capacitor C2 stores the diminished voltage when switches SW3 and SW4 are opened, and buffer 32 later transfers this voltage to the measuring circuit in the following manner. After the predetermined measuring time interval $\Delta T$, the controller 28 concurrently opens switches SW3 and SW4 and closes switch SW2, allowing the buffer 32 to access the voltage held on the measuring capacitor C2. This voltage is advanced through the buffer amplifier 32 and switch SW2 and is sampled on a sampling capacitor C2 at the input of the filter 23. The controller 28 holds switch SW2 closed for a time duration which is sufficient for a delta modulator 25 to convert the signal into a digital form. For example, a delta modulator which is capable of low current operation in an implantable device may commonly convert a signal to digital form in about 1 millisecond. One example of such a delta modulator is illustrated in U.S. Pat. No. 4,692,719 to Robert H. Whigham, entitled "Combined Pacemaker Delta Modulator and Bandpass Filter," which issued on Sep. 8, 1987 (hereinafter referred to as the "'719 patent").

Resuming consideration of an impedance measurement cycle, after delta modulator 25 converts the sample to digital form, the controller 28 opens switch SW2 and closes switch SW6 to charge measuring capacitor C2 for the next measurement cycle. In the preferred embodiment of the invention, the controller 28 measures impedance twenty times per second. For each measurement in this embodiment, the controller closes the switches SW3 and SW4 for a pulse duration of 250 ns (which initiates frequency components of about 4 megahertz), during which the voltage across the measuring capacitor C2 is placed on the antenna system 12. The resistors and capacitors associated with filter 23 pass frequencies between about 0.05 Hz and 0.8 Hz, the standard range for respiratory measurements.

When the impedance measurement circuit 14 generates measuring currents at appropriate frequencies, as will be described hereinafter, the impedance measurement reflects movements relating to respiration to a much greater extent than it does heart motion or patient motion. In addition, the impedance measurement reflects minute volume more than signals originating from other physiological and non-physiological sources because of the characteristics of filter 23. In an embodiment of the invention which filters the impedance signal to favor sensing of a respiration signal component over other components, the impedance signal is filtered by a two-pole filter with a center frequency of 0.2 Hz. The gain is reduced by a factor of two (6 dB) at frequencies of 0.05 Hz and 0.8 Hz. Alternatively, the capacitors and resistors of the circuit of filter 23 may be chosen to preferentially elicit other physiological signal components. For example, the cutoff frequencies for a bandpass filter which favors cardiac hemodynamic signals may range from 0.2 to 10 Hz. Furthermore, the cutoff frequencies for a bandpass filter which best supports patient motion signals may range from 5 to 10 Hz.

The value of the measuring capacitor C2 is selected to store the range of voltages which result from various body impedances. In one embodiment of the invention, capacitor C2 has a capacitance of 4.7 nF.

The coupling capacitor C3 provides DC isolation for the input to the measuring circuit. In one embodiment of the invention, a coupling capacitor C3 has a value of about 7.5 $\mu$F, which effectively eliminates the influence of any DC voltage on the measurement results.

As indicated earlier, the analog signal output of filter 23 passes to delta modulator 25 which provides a digital signal output on conductor 22. The digital signal output on conductor 22 is input to controller 28 for processing. Converting an analog signal to a digital representation by delta modulation is a standard technique. One example of such an operation is illustrated in the aforesaid '719 patent. The output of delta modulator 25 is a summation of a series of 0's and 1's which reflect whether the analog signal is decreasing or increasing.

Figure 2:
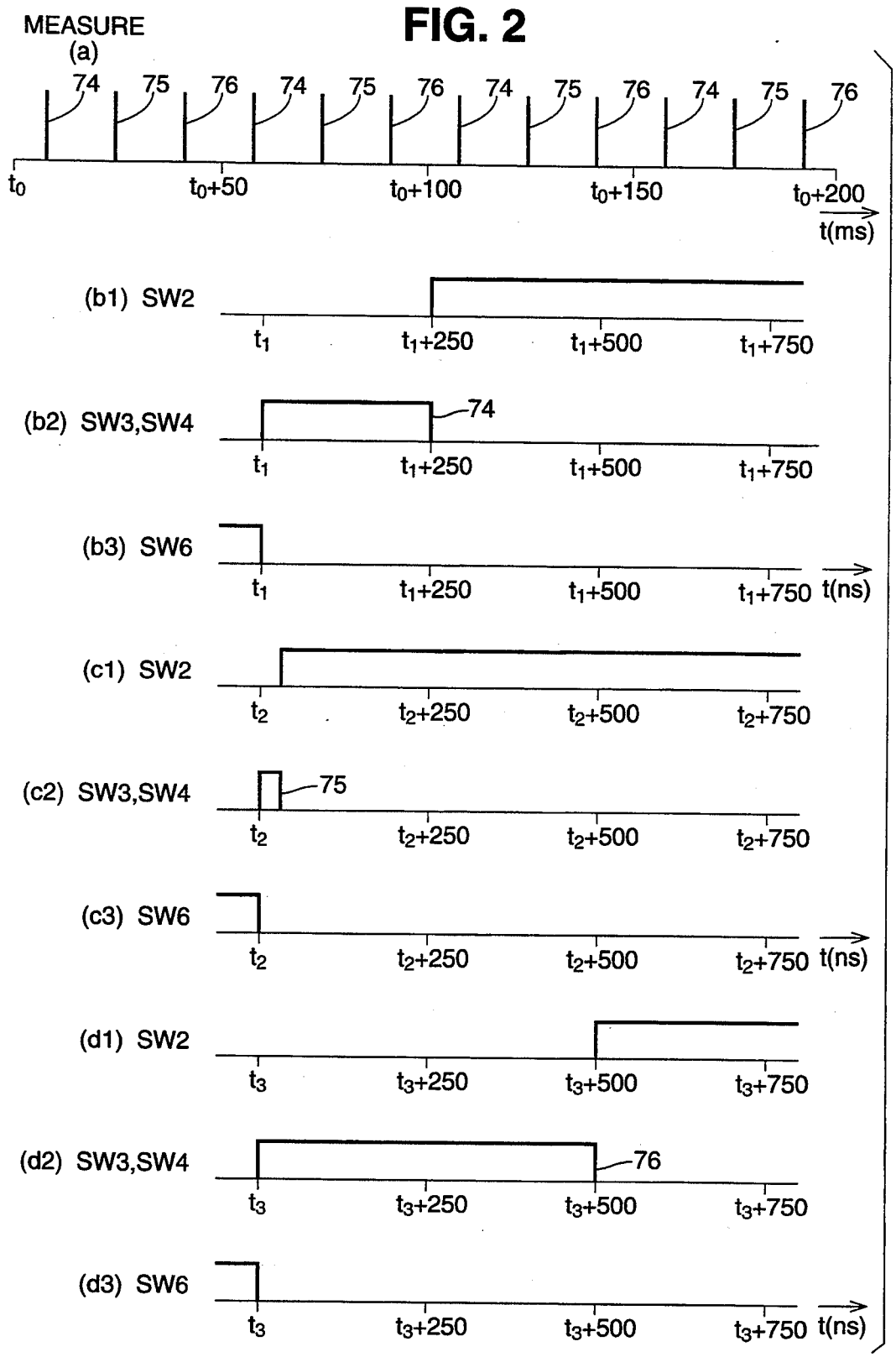
FIG. 2 shows waveform timing diagrams which are useful in understanding the operation of one implementation of an impedance measurement circuit utilized in the embodiment shown in FIG. 1.

Referring now to FIG. 2, waveform timing diagrams are shown which indicate one method by which the controller 28 may regulate switches SW2-SW4 and SW6 within the impedance measurement circuit 14 to measure three different physiological parameters—patient motion, respiration and heart motion. Referring to line (a) of FIG. 2, controller 28 samples respiration, patient motion and heart motion by means of sampling pulses 74, 75 and 76, respectively. The controller 28 regulates continuous, interleaved, sampling of each of the three physiological parameters, sequentially, at 50 millisecond intervals for each type, and with 16.67 milliseconds separating the beginning of each sample from adjacent dissimilar samples. The selection of a 50 millisecond sampling interval is made to illustrate the operation of the switches of FIG. 1 and the method of sampling. It is to be understood that other sampling intervals are intended to be included within the scope of the invention. For example, the various physiological signal components are likely to be sampled at different intervals. Cardiac hemodynamic signals may be sampled at a higher rate (e.g. 10 millisecond intervals) but only during the time blood is ejected from the heart following depolarization of the heart (e.g., from 80 milliseconds to 280 milliseconds after an R-wave).

Controller 28 has complete control of the sampling procedure. For example, the controller may enable or disable the sampling for any of the parameters, may individually change the intervals between samples relating to a particular parameter or may change the ratio of sampling for one parameter in relation to another.

Lines (b1)-(b3) of FIG. 2 illustrate one example of a procedure by which controller 28 may regulate the sampling of the respiration parameter. The controller starts the sampling procedure at $t_1$ by opening switch SW6 ((line (b3) goes low)) and closing switches SW3 and SW4 ((line (b2) goes high)) for 250 nanoseconds. Next, at $t_1+250$, the controller 28 opens switches SW3 and SW4 ((line (b2) goes low)), completing the respiration sampling pulse 74, and closes switch SW2 ((line (b1) goes high)) to allow delta modulator 25 (of FIG. 1) to convert the signal to a digital number. Switch SW2 is held closed for the time duration required to digitize the sample (for example, 1 millisecond). The controller then opens switch SW2 and closes switch SW6 (actions not shown) to finish the sampling procedure and charge the capacitor C2 (of FIG. 1).

In the same manner, lines (c1)-(c3) of FIG. 2 depict an example of the procedure by which controller 28 regulates the sampling of the patient motion parameter. The controller starts the sampling procedure at $t_2$ by opening switch SW6 ((line (c3) goes low)) and closing switches SW3 and SW4 ((line (c2) goes high)) for 25 nanoseconds (which initiates frequency components of about 40 megahertz). At the end of the 25 nanoseconds, switches SW3 and SW4 open ((line goes low)), completing the patient motion sampling pulse 75, and switch SW2 closes ((line (c1) goes high)). Switch SW2 is held closed for the time duration required to digitize the sample (for example, 1 millisecond). The controller then opens switch SW2 and closes switch SW6 (actions not shown) to finish the sampling procedure and charge the capacitor C2 (of FIG. 1).

In the same manner, lines (d1)-(d3) of FIG. 2 depict an example of the method by which the controller 28 regulates the sampling of the heart motion parameter. The controller 28 starts the sampling procedure at $t_3$ by opening switch SW6 ((line (d3) goes low)) and closing switches SW3 and SW4 ((line (d2) goes high)) for 500 nanoseconds (which initiates frequency components of about 2 megahertz). At the end of the 500 nanoseconds, switches SW3 and SW4 open ((line (d2) goes low)), completing the heart motion sampling pulse 76, and switch SW2 closes ((line (d1) goes high)). Switch SW2 is held closed for the time duration required to digitize the sample (for example, 1 millisecond). The controller then opens switch SW2 and closes switch SW6 (actions not shown) to finish the sampling procedure and charge the capacitor C2 (of FIG. 1).

Figure 3:
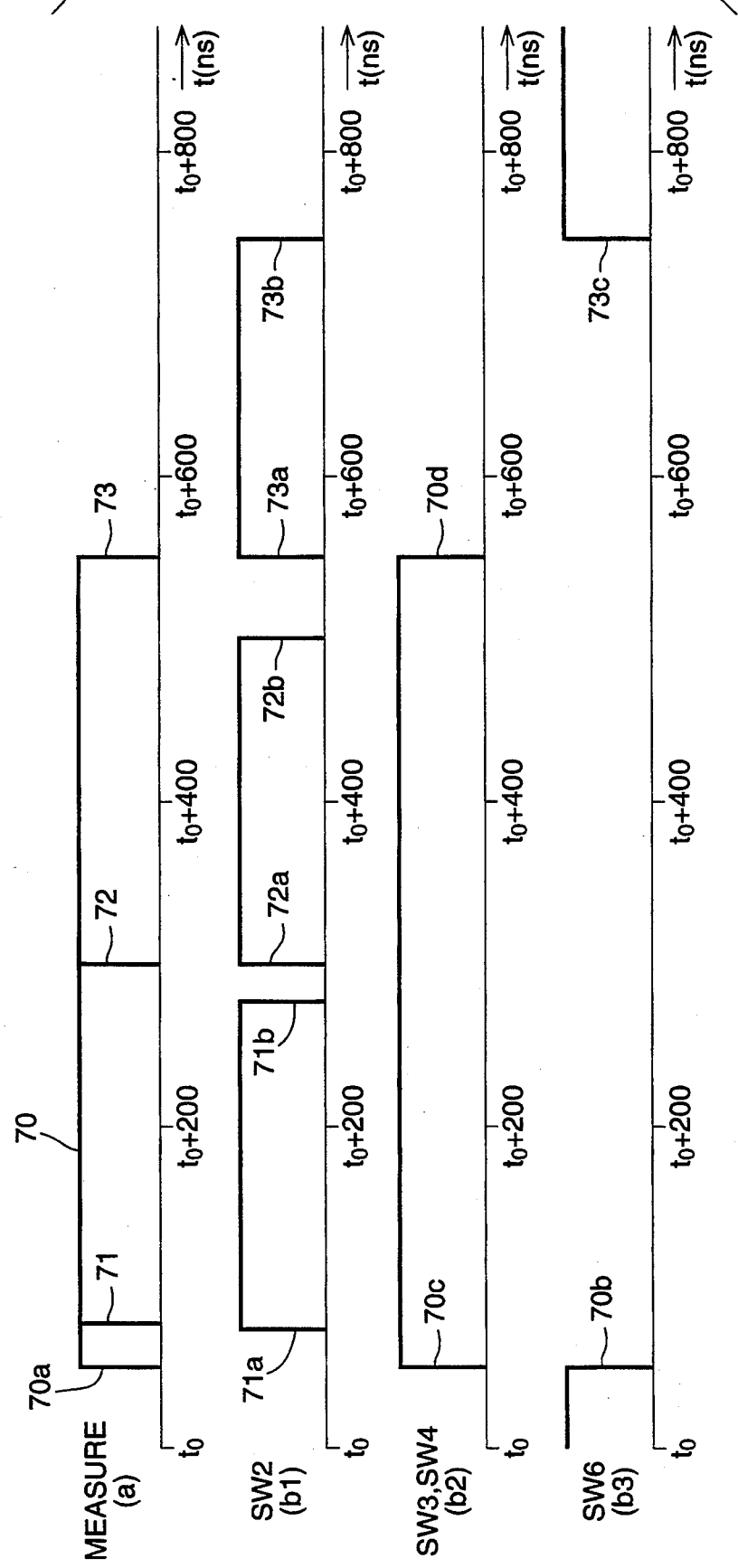
FIG. 3 illustrates waveform timing diagrams which are useful in understanding the operation of a second implementation of the impedance measurement circuit utilized in the embodiment shown in FIG. 1.

Referring now to FIG. 3, waveform timing diagrams are shown which indicate a second method by which controller 28 may regulate the switches SW2-SW4 and SW6 within the impedance measurement circuit 14 to measure the three different physiological parameters discussed with respect to FIG. 2. The method of FIG. 3 requires a much faster analog-to-digital conversion operation than does the method of FIG. 2. A delta modulator which is capable of performing the FIG. 3 method must digitize a signal in 200 nanoseconds or less. In the preferred embodiment of the invention, the faster delta modulator 25 is the delta modulator taught in the aforementioned U.S. Pat. No. 4,692,719, except that the accumulator within the delta modulator is clocked at a 320 MHz rate and reset at a 5 MHz rate, rather than, respectively, 32 kHZ and 0.5 kHz rates. Referring to line (a) of FIG. 3, the controller samples respiration, patient motion and heart motion by generating a current pulse 70, beginning at leading edge 70a and lasting a duration of 500 nanoseconds. The controller 28 then directs the measurement of patient motion, respiration and heart motion by sampling the resulting voltage at the times shown in FIG. 3 by lines 71, 72 and 73, respectively. The controller 28 may regulate continuous sampling of each of the three physiological parameters, sequentially, at preselected intervals (possibly 50 millisecond intervals, as was done in FIG. 2). In a manner similar to the description given with respect to FIG. 1, controller 28 has complete control of the sampling procedure.

Lines (b1)-(b3) of FIG. 3 illustrate one example of a procedure by which controller 28 regulates the sampling of the patient motion, respiration and heart motion parameters. The controller starts the sampling procedure by opening switch SW6 ((line (b3) goes low)), as shown at 70b, and closing switches SW3 and SW4 ((line (b2) goes high)), as shown at 70c, for a duration which is long enough to sample any of the desired parameters (for example, 500 nanoseconds to measure heart motion 73). The controller 28 times the duration of the shortest sampling measurement duration, for example 25 nanoseconds to sample the patient motion parameter 71. Next, the controller closes switch SW2, as shown at 71a, to allow the delta modulator 25 (of FIG. 1) to convert the signal to a digital number. Switch SW2 is held closed for the time duration required to digitize the sample (for example, 200 nanoseconds) and then opens, as shown at 71b. In this example, the controller 28 holds switch SW2 open for 25 nanoseconds, as shown between 71b and 72a, after which time the measuring current pulse has been applied for 250 nanoseconds, the time duration of the respiration measurement 72. Again, the controller 28 closes switch SW2, as shown at 72a, for 200 nanoseconds to allow the delta modulator 25 (of FIG. 1) to convert the signal to digital form. The controller 28 then opens switch SW2, as shown at 72b, for 50 nanoseconds, after which time the measuring current pulse has been applied for 500 nanoseconds, the time duration of the heart motion measurement 73. Next, the controller 28 opens switches SW3 and SW4 and closes switch SW2, as shown at 70d and 73a, respectively, and the delta modulator 25 (of FIG. 1) converts the heart motion signal to a digital number. Again, the controller 28 holds switch SW2 closed 200 nanoseconds. The controller 28 then opens switch SW2, as shown at 73b, and closes switch SW6, as shown at 73c, to finish the sampling procedure and charge the capacitor C2 (of FIG. 1).

From the foregoing description, it is apparent that the circuit of FIG. 1 is a component of an embodiment of the present invention in which a single sensor and circuit is capable of measuring multiple physiological parameters. The timing diagrams of FIG. 3 illustrate that the voltage arising from a single measuring current pulse may be sampled at various times to measure distinct and separate physiological parameters.

Referring to FIG. 4, an embodiment of the impedance measurement circuit 14, which operates in a manner similar to the circuit of FIG. 1, is shown. This embodiment of the alarm 5 incorporates an impedance measurement circuit 14 having three individual signal processing paths for processing the three different types of physiological information. The impedance measurement circuit 14 includes a connection through a switch SW4 with the housing 30, and connections through switches SW3, SW13 and SW23 with the antenna system 12. Buffers 32, 41 and 43 and filters 23, 34 and 39 are also employed in circuit 14.

All switches in FIG. 4 are controlled by controller 28. One output line 33 of the controller is shown extended to switch SW2, but it is to be understood that the switches SW3, SW4, SW5, SW6, SW12, SW13, SW16, SW22, SW23 and SW26 are similarly controlled. The controller closes switches SW6, SW16 and SW26 to charge measuring capacitors C2, C4 and C5 to a regulated voltage source VDD. Subsequently, the controller opens switches SW6, SW16 and SW26 and closes switches SW3 and SW4, while holding switch SW5 open, for a predetermined measuring interval $\Delta T_1$, thereby connecting capacitor C2 to antenna system 12 through coupling capacitor C3. While the switches SW3 and SW4 are closed, measuring capacitor C2 discharges through capacitor C3 into the antenna system 12, thereby decreasing the voltage across measuring capacitor C2. The amount by which the voltage across the measuring capacitor C2 diminishes depends on the impedance of the surrounding tissue. The impedance of the surrounding tissue is the object of the measurement.

Measuring capacitor C2 stores the diminished voltage and buffer 32 transfers this to the measuring circuit in the following manner. After the predetermined measuring time interval $\Delta T_1$, the controller 28 concurrently opens switches SW3 and SW4 and closes switch SW2, allowing the buffer 32 to access the voltage held on the measuring capacitor C2. This voltage is advanced through the buffer amplifier 32 and switch SW2, and is sampled on sampling capacitor C1 at the input of the filter 23. The controller 28 holds switch SW2 closed for a time duration which is sufficient for delta modulator 25 to convert the signal into a digital form. After converting the sample to digital form, the controller 28 opens switch SW2 and closes switch SW6 to charge measuring capacitor C2 for the next measurement cycle.

Next, the controller 28 closes switches SW13 and SW4, while holding switch SW5 open, for a second predetermined measuring interval $\Delta T_2$, thereby connecting measuring capacitor C4 to antenna system 12 through the coupling capacitor C3. While the switches SW13 and SW4 are closed, measuring capacitor C4 discharges through coupling capacitor C3 into the antenna system 12, thereby decreasing the voltage across capacitor C4. Measuring capacitor C4 stores the decreased voltage and buffer 41 transfers this voltage to the measuring circuit in the following manner. After the predetermined measuring time interval $\Delta T_2$, the controller 28 concurrently opens switches SW13 and SW4 and closes switch SW12, allowing the buffer 41 to access the voltage held on the measuring capacitor C4. This voltage is advanced through the buffer amplifier 41 and switch SW12, and is sampled on sampling capacitor C6 at the input of the filter 34. The controller 28 holds switch SW12 closed for a time duration which is sufficient for delta modulator 25 to convert the signal to digital form. After converting the sample to digital form, the controller 28 opens switch SW12 and closes switch SW16 to charge measuring capacitor C4 for the next measurement cycle.

Next, the controller 28 closes switches SW23 and SW4, while holding switch SW5 open, for a third predetermined measuring interval $\Delta T_3$, thereby connecting measuring capacitor C5 to antenna system 12 through the coupling capacitor C3. While the switches SW23 and SW4 are closed, measuring capacitor C5 discharges through capacitor C3 into the antenna system 12, thereby decreasing the voltage across capacitor C5. Measuring capacitor C5 stores the decreased voltage and buffer 43 transfers this voltage to the measuring circuit in the following manner. After the predetermined measuring time interval $\Delta T_3$, the controller 28 concurrently opens switches SW23 and SW4 and closes switch SW22, allowing the buffer 43 to access the voltage held on the measuring capacitor C5. This voltage is advanced through the buffer amplifier 43 and switch SW22, and is sampled on sampling capacitor C7 at the input of the filter 39. The controller 28 holds switch SW22 closed for a time duration which is sufficient for delta modulator 25 to convert the signal to digital form. After converting the sample to digital form, the controller 28 opens switch SW22 and closes switch SW26 to charge measuring capacitor C5 for the next measurement cycle.

In one embodiment of the invention, the controller 28 measures each physiological parameter twenty times per second. The time duration $\Delta T_1$ is 25 nanoseconds (which initiates frequency components of about 40 megahertz) and the voltage measured on capacitor C2 represents a patient motion parameter. The time duration $\Delta T_2$ is 250 nanoseconds (which initiates frequency components of about 4 megahertz) and the voltage measured on capacitor C4 represents a respiration parameter. The time duration $\Delta T_3$ is 500 nanoseconds (which initiates frequency components of about 2 megahertz) and the voltage measured on capacitor C5 represents heart motion. The operations of filter 23, capacitor C1 and delta modulator 25 are the same in FIG. 1 and FIG. 4.

The filter 23 preferably filters the impedance signal in such a manner as to favor the sensing of a cardiac hemodynamic signal component over other physiological and nonphysiological signal components. To this end, filter 23 filters the impedance signal using a two-pole filter with a center frequency of 1.4 Hz. The gain of filter 23 is reduced by a factor of two (6 dB) at frequencies of 0.2 Hz and 10 Hz.

The filter 34 preferably filters the impedance signal in such a manner as to favor the sensing of a respiration signal component over other physiological and nonphysiological signal components. To this end, filter 34 filters the impedance signal using a two-pole filter with a center frequency of 0.2 Hz. The gain of filter 34 is reduced by a factor of two (6 dB) at frequencies of 0.05 Hz and 0.8 Hz.

The filter 39 preferably filters the impedance signal in such a manner as to enhance the sensing of a patient motion signal component. To this end, filter 39 filters the impedance signal using a two-pole filter with a center frequency of about 6 Hz. The gain of filter 34 is reduced by a factor of two (6 dB) at frequencies of 5 Hz and 10 Hz.

Figure 5:
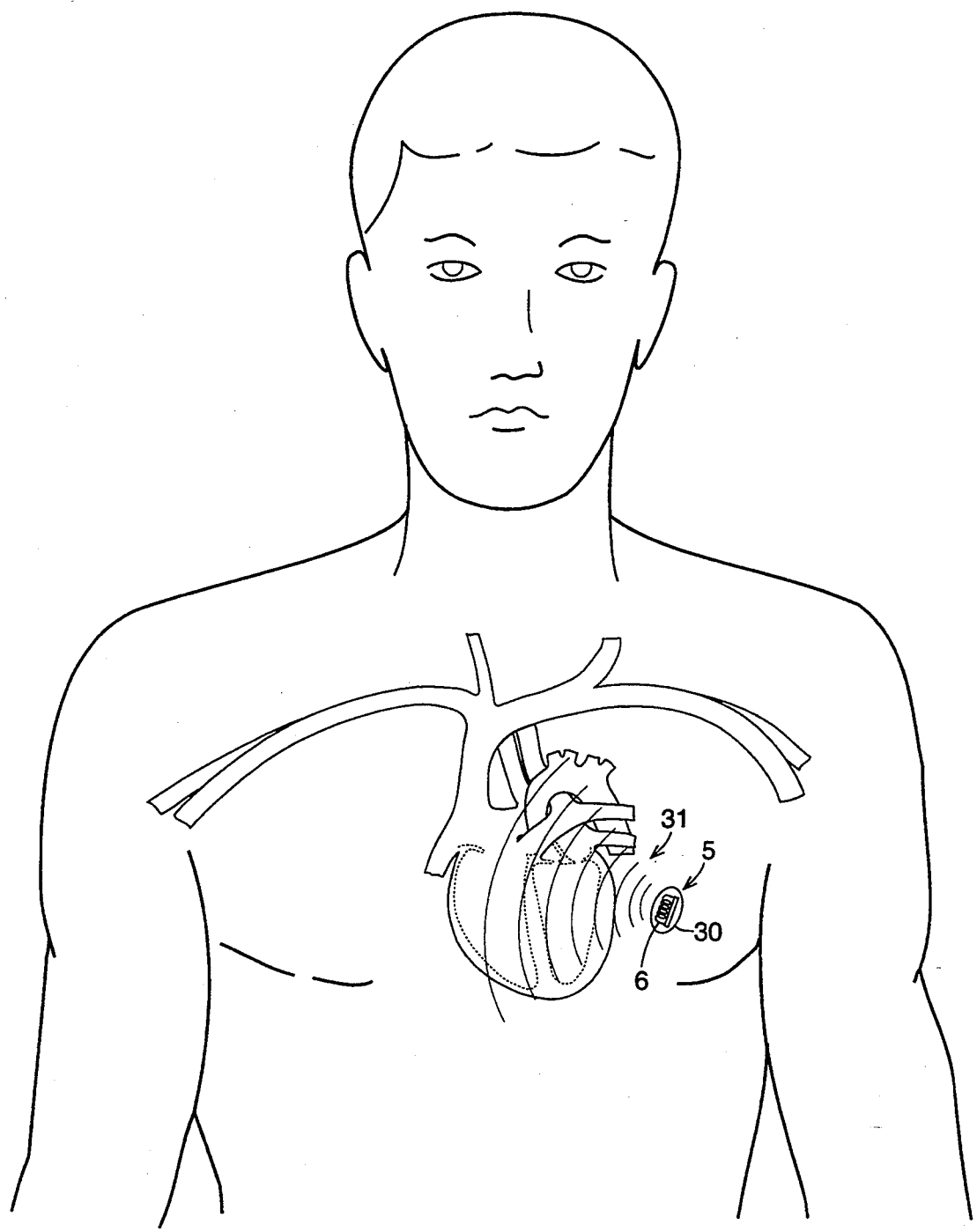
FIG. 5 is an illustration which depicts one location for placement of the implantable cardiac arrhythmia alarm within a patient's body.

FIG. 5 is an illustration depicting a manner of locating the implantable cardiac arrhythmia alarm 5 within a patient's body so that the impedance-sensing antenna coil 6 positioned within its housing 30 is oriented to radiate its electrical field, shown generally at 31, toward the patient's pleural area.

Figure 6:
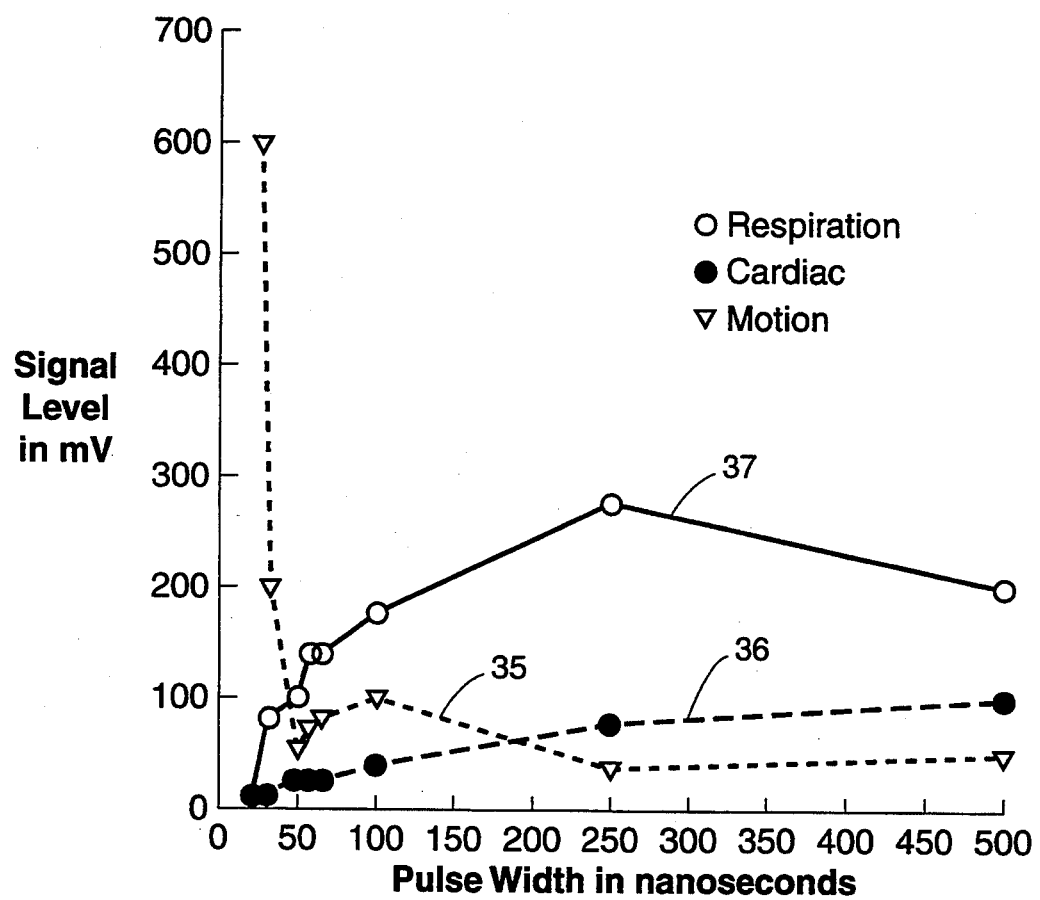
FIG. 6 is a graph which characterizes the relative levels of different signals which are detected by the circuit of FIG. 7 when it interrogates a patient's body by applying current pulses of various pulse widths to an antenna.
Figure 7:
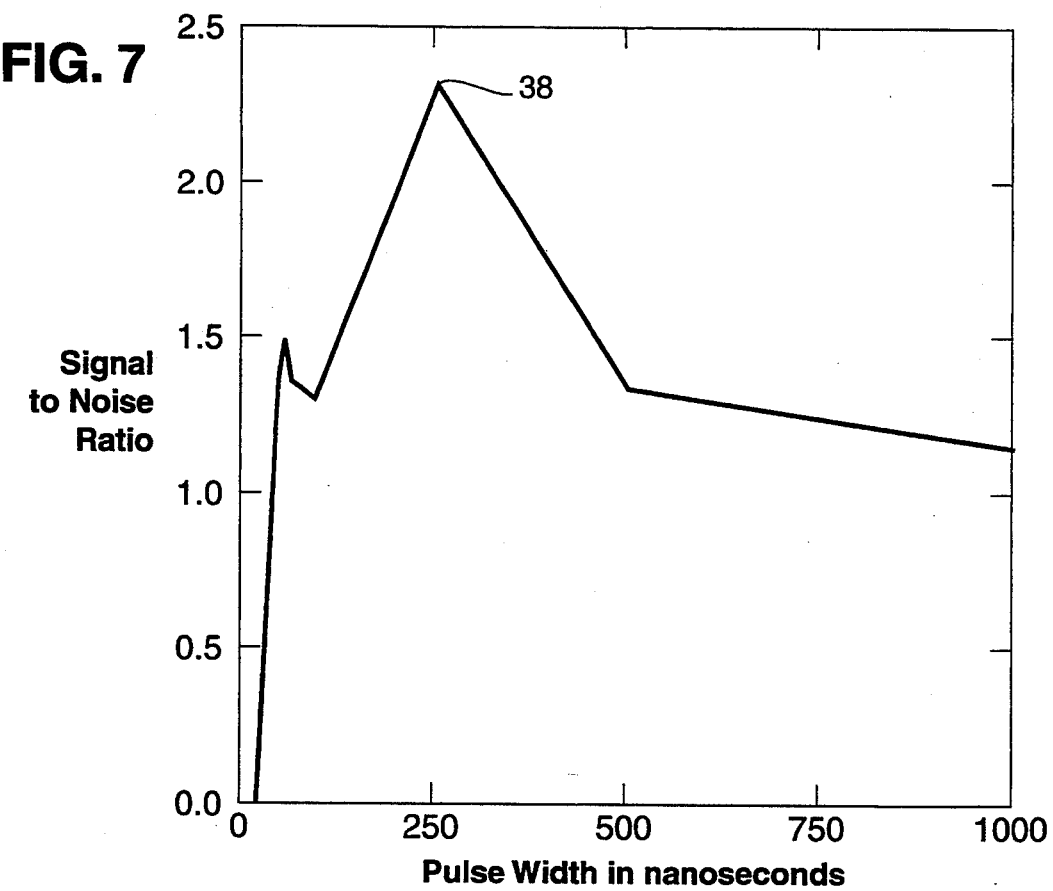
FIG. 7 is a graph which illustrates the level of a respiration signal, shown in FIG. 6, relative to a combination of other motion signals, shown in FIG. 6, as such signals are detected by the circuit of FIG. 1 when it interrogates a patient's body by applying current pulses of various pulse widths to an antenna.

The graph of FIG. 6 characterizes the relative levels of motion signals, including patient, heart and respiration motion, which are detected by the circuit of FIG. 1 when it interrogates a patient's body with current pulses of different widths. It illustrates an important advantage of the alarm 5 of the present invention. The alarm can "tune" the impedance sensor to measure a particular type of signal and reject unwanted signals and other noise by selecting a particular measuring current pulse width. At very short pulse widths (e.g., 25 to 200 nanoseconds) patient motion artifact signals are easily distinguishable from other signals, such as the signals arising from respiration and heart motion. The "motion" curve 35 of FIG. 6 illustrates that the shortest pulse widths, limited in brevity by technical feasibility alone, give rise to body motion signal amplitudes that are larger than signal amplitudes arising from respiratory and cardiac motion for pulse widths up to approximately 50 nanoseconds. From 50 to about 200 nanoseconds, the amplitude of the impedance signals relating to body motion gradually decreases while the amplitudes of signals relating to respiratory and cardiac motion gradually increase. In this range, it is more difficult to distinguish the motion signal from respiratory and cardiac motion signals, although the signals can be distinguished by the additional filtering, discussed hereinbefore, provided by filter 39 of FIG. 4. Similarly, the amplitude of physiological signals arising from the heart's activity steadily rises with increasing pulse width duration to a maximum at 500 nanoseconds, as shown by "cardiac" curve 36. Further, the amplitude of respiratory signals abruptly rises with pulse duration increases to a pulse width of about 250 ns, then decreases for larger pulse width durations, as shown by "respiratory" curve The respiration-measuring portion of the alarm of the present invention seeks a preferred pulse width of about 250 ns, which provides the best respiratory signal to noise ratio, as is illustrated at 38 in FIG. 7. FIG. 7 comprises a graph that illustrates the level of a desired respiratory signal of FIG. 6 relative to a combination of non-respiration "noise" signals of that figure. A pulse width of this duration (250 ns) lessens the influence of cardiac signal "noise" avoids interface electrolytic phenomena and reduces the influence of patient motion artifacts.

Figure 8:
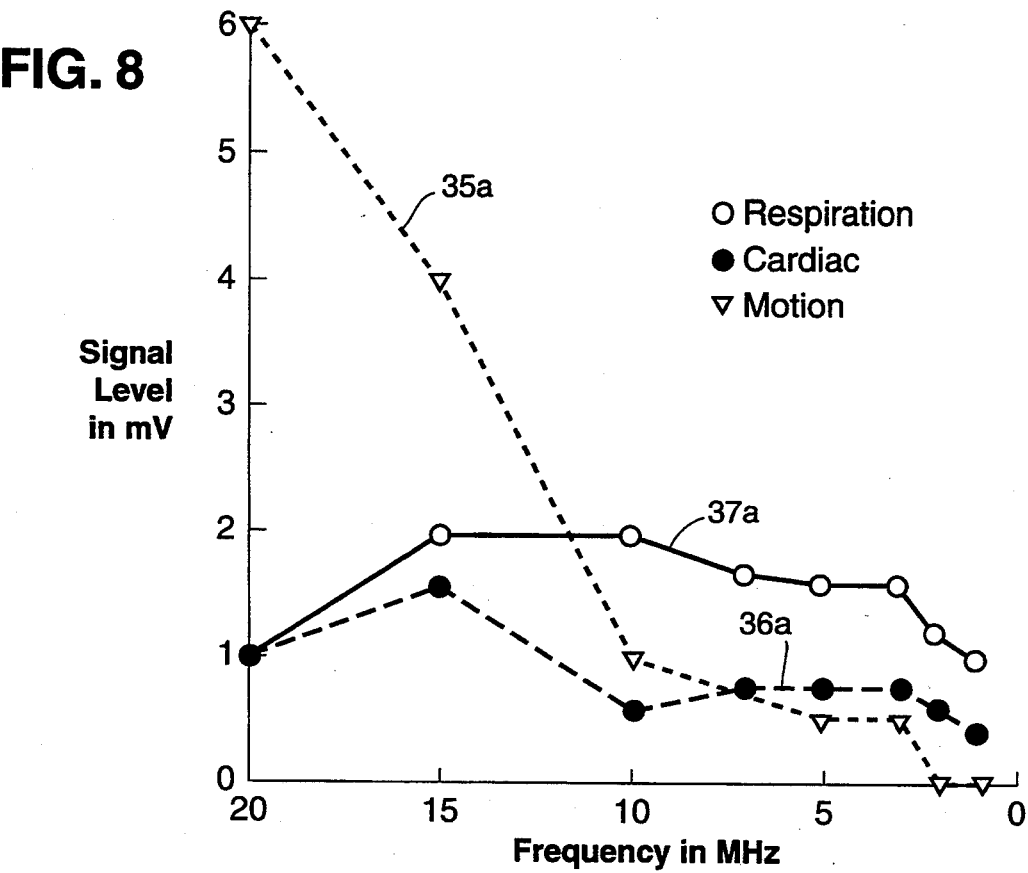
FIG. 8 is a graph which characterizes the relative levels of different physiological and nonphysiological signals as detected by an impedance measurement circuit which interrogates a patient's body with various frequencies of sinusoidal-like oscillating current or timed pulses of sinusoidal-like oscillating current.

FIGS. 6 and 7 exemplify how different pulse widths provide for differentiation of signals arising from various origins. Similarly, FIG. 8 illustrates this phenomenon in a sensing system which employs sinusoidal-like oscillating current modulation, rather than discrete current pulses. Shorter pulse widths in a pulsed system have a similar effect upon signal sensing as higher frequencies in a sinusoidal-like oscillating current system. In general, the alarm 5 provides the best respiration signal sensing, in comparison with cardiac and motion noise, when the measuring current frequency is about 2 MHz. At higher frequencies, motion artifacts are large and at lower frequencies, cardiac signals obscure the respiration signal.

The graph of FIG. 8 illustrates the signal amplitude arising from various sources as a function of measuring sinusoidal-like oscillating current frequency. "Motion" curve 35a represents the amplitude of patient motion artifact signals; "cardiac" curve 36a represents the amplitude of physiological signals arising from the heart; and "respiration" curve 37a represents the amplitude of respiratory signals. The alarm may deliver these oscillating measuring currents in the form of sinusoidal-like oscillating waves or in the form of timed pulses of oscillating waves. Timed pulses of oscillating waves are discontinuous bursts of oscillating waves which last for a predetermined duration. For example, respiration may be measured by applying a 10 MHz oscillating wave burst lasting a duration of 100 ms. The measurements resulting from both methods are practically the same. To provide timed pulses of sinusoidal-like oscillating measuring current, the alarm deactivates the oscillating current to conserve energy. The duration of timed pulses of sinusoidal-like oscillating current may range from one cycle of the oscillating frequency to essentially an infinite duration.

Figure 9:
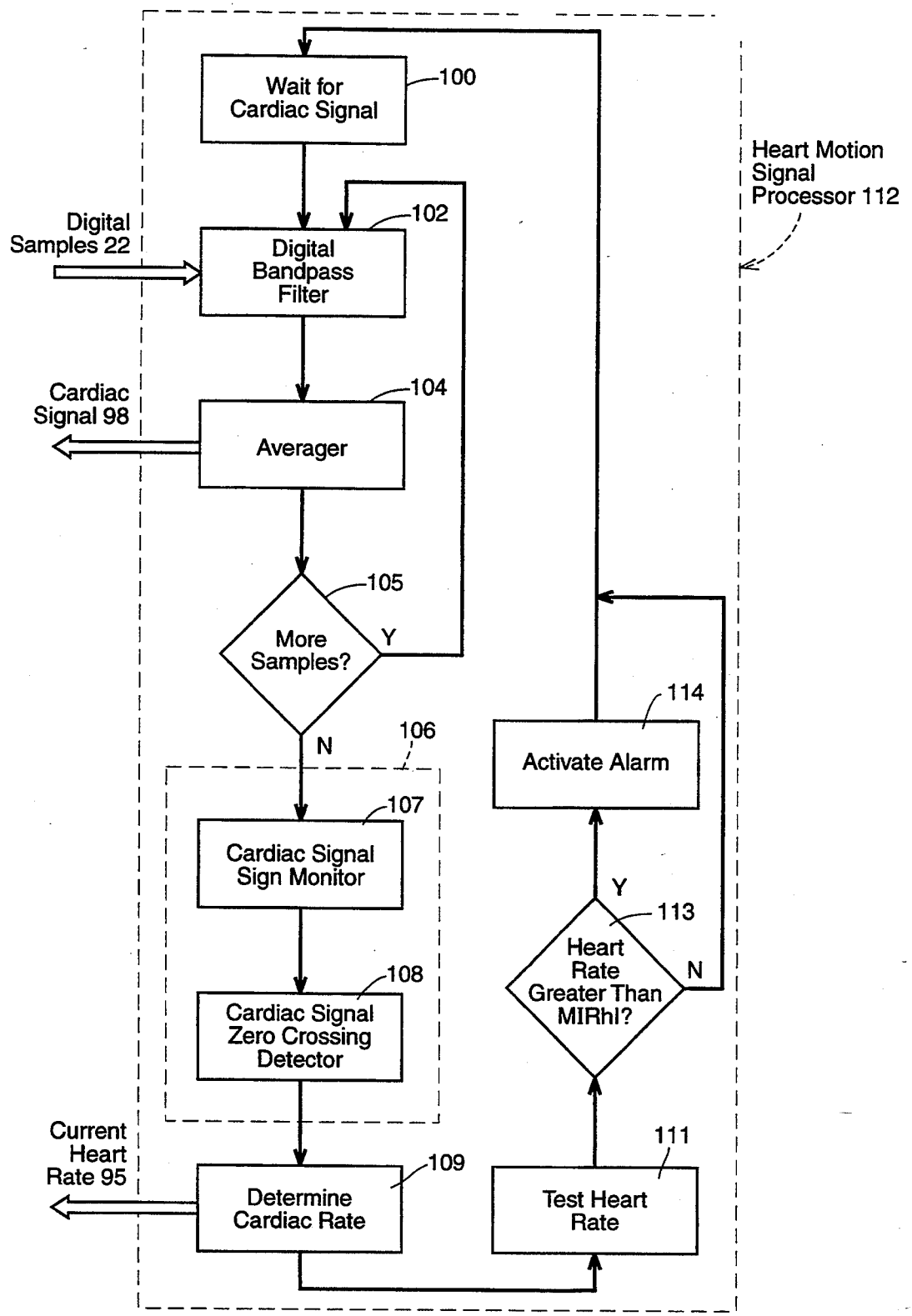
FIG. 9 depicts circuit blocks, contained in a controller shown in block form in FIG. 1, which operate on digital samples of the impedance measurement to derive a physiological parameter based on a heart motion.

Referring now to the flow chart of FIG. 9, designated generally as a heart motion signal processor 12, the functional blocks performed by controller 28 are shown in greater detail. The flow chart illustrates the manner in which the controller 28 analyzes digital samples, provided via conductor 22 from the impedance measurement circuit 14 of FIGS. 1 or 4, and derives the value of a cardiac signal 98 which is indicative of the patient's heart motion. Referring to FIG. 1 in conjunction with FIG. 9, in wait-for-cardiac-signal block 100, the controller 28 sets the interval between successive sensor samples and then waits for a timing signal indicating that a heart motion signal sample is due. The controller 28 controls the sampling rate of the digital samples. A preferred sampling rate is approximately 100 Hz, although the controller 28 can regulate the sampling rates in the range of from 20 Hz to 200 Hz. The preferred sampling time interval is 10 milliseconds, although the controller 28 can set this interval to range from 5 milliseconds to 50 milliseconds. Upon the occurrence of this timing signal, the controller 28 activates the impedance measurement circuit 14 to acquire a raw heart motion signal. The heart motion signal processor 12 reads digital samples on conductor 22 and applies them to a digital bandpass filter 102 which rejects low and high frequency components of the digital signal. An averager block 104 sums or digitally integrates the digital sample value over a selected time period to determine a time average of the heart motion signal.

Averager block 104 counts the number of samples processed by the digital bandpass filter 102 and averager block 104 to correlate the same with the heart motion signal time period. If more samples are to be processed in this cardiac cycle, more-samples? logic block 105 returns control of the procedure to the digital bandpass filter 102 to process another sample. Otherwise, the heart motion signal processor 112 determines the current heart rate. The alarm 5, upon request from an external communicating device, may transmit the cardiac signal 98, the output signal from the averager 104, to such device for patient motion signal monitoring and analysis. The heart motion signal processor may be activated by the controller 28 by a request from an external communicating device to provide heart motion data for analysis by the device. The heart motion signal processor 112 evaluates the cardiac signal 98 produced from the averager 104 to determine the patient's current heart rate 95 in a heart rate analyzer 106, including a cardiac signal sign monitor 107 and a cardiac signal zero crossing detector 108. The cardiac signal sign monitor 107 tests the signs of the digital samples of the cardiac signal 98 produced by the averager 104 to detect zero crossings, indicating heart rate. The cardiac signal sign monitor 107 delivers successive bits, each of which represents the sign of a digital sample, to the cardiac signal zero crossing detector The zero crossing detector 108 senses heart rate according to the timing of polarity changes of the cardiac signal 98.

Zero crossings are not registered if they occur at a higher rate than is physiologically possible. Zero crossings occurring more frequently than this limit merely indicate the presence of noise. Therefore, the cardiac signal zero crossing detector 108 counts the number of samples having a negative sign and the number of samples having a positive sign in a predefined number of consecutive samples. To constitute a zero crossing a preset preponderance of samples must have a particular sign and the preponderance of samples found at the last determined zero crossing must have the opposite sign. The range of physiological heart rates, the sampling frequency of the cardiac signal and the fidelity of the signal determine the number of samples analyzed and the proportion of those samples having a particular sign. Thus, for example, if a physiological heart rate may be no faster than 200 bpm and the heart signal sampling rate is 33.3 Hz (samples are taken at 30 ms intervals), 7 out of 10 samples may be required to define a zero crossing. Thus, at least 70% of the most recent samples in the last 0.3 second must have a sign opposite to that of the sign determined after the last zero crossing to define a new zero crossing. When the sign changes, the determine-cardiac-rate block 109 sets the current heart rate 95 value on the basis of the timing of zero crossings determined by the cardiac signal zero crossing detector 108. An alternative heart signal analyzer (not shown) to analyzer 106 may employ a highpass filter to remove heart signal noise, a threshold detector (or comparator) and a trigger to identify a heartbeat.

The heart motion signal processor 112 compares the current heart rate 95 to a rate limit indicative of an abnormal heart in test-heart-rate block 111. This rate limit may be a programmed rate or, if an automatic rate limit setting (not shown) is selected, the rate limit may be a metabolic indicator rate high limit (MIRhl) based on respiration (MIRhl$_R$) or on patient motion (MIRhl$_{PM}$). If, under control of heart-rate-greater-than-MIRhl logic block 113, the current heart rate 95 is faster than MIRhl, then the controller 28 actuates the alarm annunciator 130, shown in FIGS. 1 or 4, in activate-alarm block 114.

In addition to heart motion signals, the impedance measurement block 14 of FIGS. 1 and 4 also may acquire signals relating to the patient's respiration. With respect to these respiration signals, the impedance measurement block 14 derives digital impedance samples, in the form of 8-bit data bytes determined at a rate of 20 per second, and communicates these samples to a respiration signal processor 78 (FIG. 10) via conductor 22. Negative digital signals on the conductor 22 indicate a decreasing analog respiration signal. Positive digital signals signify an increasing respiration signal.

Figure 10:
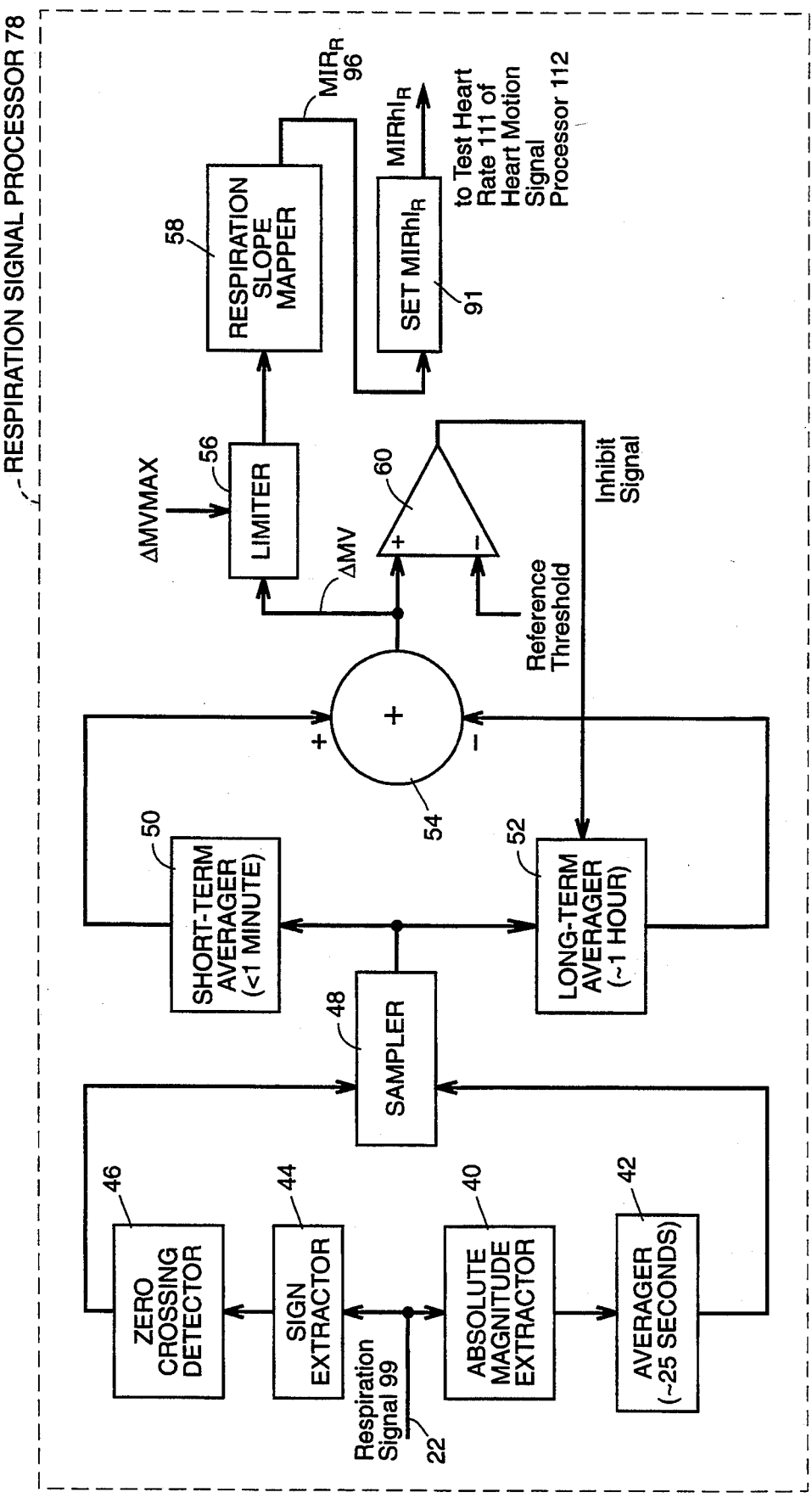
FIG. 10 depicts circuit blocks, contained in a controller shown in block form in FIG. 1, which operate on digital samples of the impedance measurement to derive a physiological parameter based on a respiration.

Referring to FIG. 10, when the impedance measurement block 14 is configured by the controller 28 to perform a respiration measurement, the digital signal on conductor 22 is called the respiration signal 99. FIG. 10 illustrates functional blocks of respiration signal processor 78 that perform a method for deriving a respiration signal from the digital samples provided by impedance block 14. The respiration signal processor 78 may be activated by the controller 28 via a request from an external communicating device, either to provide respiration data for analysis by the device or to activate an "automatic respiration alarm threshold" function. An absolute magnitude extractor 40 derives the absolute magnitude of each digital sample (i.e., negatively signed samples are changed to positive samples of the sample amplitude). The average value of the digital samples is zero because the filter 23 (FIG. 1) in the impedance measurement block 14 has a gain of zero for a DC input. By eliminating the sign from all samples, an averager 42 derives a running average of the absolute magnitudes of the samples.

The output of the averager 42 is a measure of the patient's respiratory volume (the volume of air exchanged by the lungs) and is used to derive the patient's respiratory minute volume which, in turn, may be used to determine a heart rate indicative of the patient's metabolic demand. The time constant of the averager 42 is short (e.g., about 25 seconds) so that its digital output value represents the average respiratory tidal volume over a few breaths. The absolute magnitude value of each sample represents the respiratory impedance signal. The respiration signal processor 78 adds and averages a sequence of absolute magnitude samples to reflect the patient's respiratory tidal volume.

A sign extractor 44 monitors the signs of the digital samples on conductor 22 to detect zero crossings indicating respiratory rate. The sign extractor 44 delivers successive bits, each of which represents the sign of a digital sample, to a zero crossing detector 46. The zero crossing detector 46 senses respiration rate according to the timing of polarity changes of the impedance measurement signal. Generally, a zero crossing occurs whenever the signs of a digital sample and its immediately preceding sample differ. However, zero crossings occurring at a rate higher than is possible physiologically, in accordance with a predetermined physiological limit, indicates a noisy respiration signal. Thus, the zero crossing detector 46 analyzes the signs of a number (for example, 10) of the most recently acquired samples and determines whether a defined preponderance of samples (for example, 7 of 10) have a particular sign. If so, and if the last zero crossing operation which found a preponderance of a particular sign determined that the majority had an opposite sign, the zero crossing detector 46 presumes the occurrence of a zero crossing. Thus, at least 70% of the most recent samples in the last 0.5 second must have a sign opposite to that of the sign determined after the last zero crossing to define a new zero crossing.

When the sign changes, the zero crossing detector 46 triggers a sampler 48 to read the current average value presented by the averager 42. The sampler 48 delivers this average value to both a short-term averager 50 and a long-term averager 52. Preferably, the time constant of the short-term averager 50 is about a minute and the time constant of the long-term averager 52 is about an hour. Twice during each breath, when the impedance signal crosses zero during exhalation and during inhalation, the zero crossing detector 46 pulses its output and the sampler 48 samples.

Each average value sample at the output of averager 42 represents the tidal volume, the average of the last few integrals of the respiratory impedance signal. The short-term averager 50 and the long-term averager 52 derive values which depend not only on the magnitudes of the samples, but also upon the rate of the oscillating respiratory signal, as determined by the zero crossing detector 46. Because the long-term and short-term averagers update and accumulate samples at each zero crossing event, the long-term and short-term minute volume values reflect the rate of breathing as well as the depth, or volume, of breathing.

A summer 54 derives a signal $\Delta MV$, which is the difference between the short-term averaged and long-term averaged minute volume signals. The signal $\Delta MV$ is a control signal which is used to compute a metabolic demand heart rate $MIR_R$. As the short-term average increases relative to the long-term average (i.e., as $\Delta MV$ increases), representing an increasing metabolic demand, the metabolic demand heart rate $MIR_R$ increases. Conversely, when $\Delta MV$ decreases, the metabolic demand rate $MIR_R$ decreases.

The $\Delta MV$ value at any instant is the input to a limiter 56, which compares $\Delta MV$ to $\Delta MVMAX$, a predetermined value which serves as the maximum $\Delta MV$ value allowed to control the metabolic demand heart rate $MIR_R$. The limiter 56 applies the current value of $\Delta MV$, or $\Delta MVMAX$ if it is smaller than $\Delta MV$, to the input of a respiration slope mapper 58. The respiration slope mapper 58 compares the output of limiter 56 to a table of $\Delta MV$ values, each of which is correlated to a heart rate value so that increasing values of $\Delta MV$ are mapped into faster heart rates. The table may be set via telemetry, using an external programmer and analyzer 220 shown in FIG. 12. The slope mapper 58 continuously presents its output, a difference value called a respiration-based metabolic indicator heart rate ($MIR_R$) 96, to set-$MIRhl_R$ block 91, which determines the high rate limit of a respiration-based metabolic indicator heart rate $MIRhl_R$. A current heart rate 95 (FIG. 9) faster than $MIRhl_R$ is considered abnormal. The current heart rate 95 may be compared to $MIRhl_R$ in test heart rate block 111 of FIG. 9 and, if it is faster, the controller 28 actuates the alarm annunciator 130, shown in FIGS. 1 or 4, in activate alarm block 114 (FIG. 9).

Many conventional implantable devices, such as pacemakers, include a telemetry receiver/transmitter 68 (FIG. 1) which allows a physician to program into the device parameters such as minimum rate, $\Delta MVMAX$ and a reference threshold which is applied to a comparator 60, as will be described below. One method of deriving these programmable parameters is disclosed in the aforementioned U.S. Pat. No. 4,901,725.

Resuming consideration of FIG. 10, the output of summer 54 is input to the limiter 56 and also to the plus input of comparator 60. The telemetrically-programmed reference threshold feeds the minus input of the comparator. Whenever $\Delta MV$ exceeds the reference threshold, the output of the comparator goes high and inhibits the long-term averager 52. In effect, a large value of $\Delta MV$ represents a metabolic demand which is associated with an exercising patient. Until the patient stops exercising, the long-term average does not increase. If it were allowed to increase, after an hour or more the long-term average would approach the value of the short-term average, $\Delta MV$ would diminish and the metabolic demand heart rate $MIR_R$ would drop from its original high value. Once the patient begins exercising and the heart rate increases, it is not desirable that the rate decrease simply due to the elapse of time. For this reason, the alarm fixes the long-term average. When the patient stops exercising and the short-term average decreases, $\Delta MV$ will fall below the reference threshold and the long-term average will again track the short-term average in the usual manner. In the illustrative embodiment of the invention, the reference threshold is equal to one-half of $\Delta MVMAX$, unless the physician programs the value differently. This technique allows long-term adaptation to a basal minute volume measurement level while still allowing extended periods of exercise.

Figure 11:
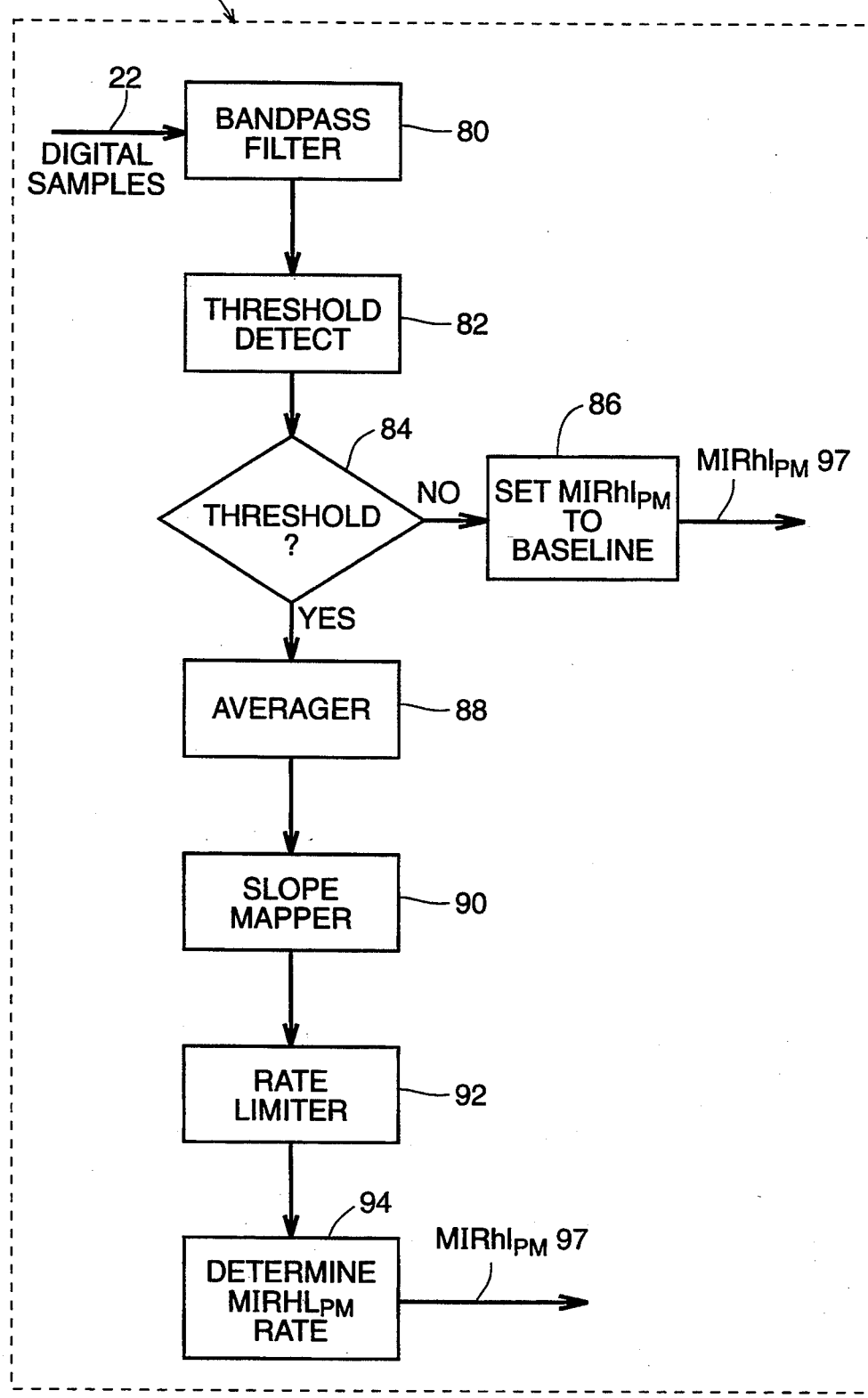
FIG. 11 depicts circuit blocks, contained in a controller shown in block form in FIG. 1, which operate on digital samples of the impedance measurement to derive a physiological parameter based on a patient motion.

Referring now to the flow chart of FIG. 11, designated generally as a patient motion signal processor 79, the functional blocks performed by controller 28 are shown in greater detail. The patient motion signal processor 79 may be activated by the controller 28, via a request from an external communicating device, either to provide patient motion data for analysis by the device or to activate an "automatic patient motion alarm threshold" function. The automatic patient motion alarm threshold function measures a quantitative patient motion parameter, converts the patient motion parameter to a metabolic indicator heart rate ($MIR_{PM}$), sets a metabolic indicator heart rate high limit ($MIRhl_{PM}$) as a function of $MIR_{PM}$ and compares the current measured heart rate to $MIRhl_{PM}$ to determine whether the alarm should be activated. The flow chart of FIG. 11 illustrates the manner in which the controller 28 derives the value of patient motion from digital samples provided via conductor 22 from the impedance measurement circuit 14 of FIGS. 1 and 4. The patient motion signal processor 79 reads the digital samples on conductor 22 and applies them to a bandpass filter 80 to reject low and high frequency components of the digital signal. The alarm 5 may be activated by a request from an external communicating device to transmit the output signal from the bandpass filter 80 to the external device for patient motion signal monitoring and analysis.

A threshold-detect block 82 compares the filtered signal amplitude to a preset threshold value. Under the control of a threshold logic block 84 and a set-MIRhl$_{PM}$-to-baseline block 86, if the signal filtered does not surpass the threshold value, a metabolic indicator rate high limit MIRhl$_{PM}$ rate 97 is set to a predetermined baseline rate. If the filtered signal is larger than the threshold value, the rate 97 is derived as follows. Averager block 88 sums or digitally integrates the digital sample values over a selected time period to determine a time average of the patient motion signal. Next the averaged signal is input to a slope mapper 90 to convert the current processed patient motion sample value to a metabolic indicator heart rate high limit (MIRhl$_{PM}$) value, according to a predetermined and selected linear or nonlinear slope relationship. This slope relationship takes into account the conversion of the patient motion signal to a metabolic indicator heart rate (MIR$_{PM}$) in addition to setting the metabolic indicator heart rate high limit (MIRhl$_{PM}$) as a function of MIR$_{PM}$. A rate-limiter block 92 compares this MIRhl$_{PM}$ rate to a preselected upper limit and, if the rate is above this limit, will set MIRhl$_{PM}$ to such limit. The derived MIRhl$_{PM}$ rate 97 is set in determine-MIRhl$_{PM}$ block 94. The current heart rate 95 may be compared to the derived MIRhl$_{PM}$ rate 97 in test-heart-rate block 111 of FIG. 9 and, if it is faster, the controller 28 actuates the alarm annunciator 130, shown in FIGS. 1 or 4, via activate-alarm block 114 of FIG. 9.

Telemetric programming by a physician may be used to program the selected time period, slope, upper and lower rate limits and rate smoothing variables.

The system of the preferred embodiment of the invention may include a number of physically separate components, some implantable and others non-implanted. In a particular application, some of the components may not be clinically necessary and are optional. Referring to FIG. 12, illustrated system components are an implantable cardiac arrhythmia alarm 5, including a telemetry receiver/transmitter 68, an external programmer and analyzer 280, a personal communicator alarm device 230, a telephonic communicator 240 which communicates with an external programmer and analyzer 260 in a health care provider's office using a transtelephonic decoder or modem 270, a full disclosure recorder 250, an external antitachycardia pacemaker or defibrillator (not shown), and a percutaneous or external drug infusion pump (not shown). The telephonic communicator 240 may be a cellular telephone link. The implantable cardiac arrhythmia alarm 5 and the external programmer and analyzer 220 are mandatory system components. The need for other components depends on the medical application at hand or objectives of a clinical investigation. All components, other than the implanted alarm 5, must include at least a telemetry receiver for receiving data control signals from the implantable cardiac arrhythmia alarm 5.

The external programmer and analyzer 220 is similar to prior art cardiac pacemaker programmers that are capable of recording data from cardiac pacemakers. The external programmer and analyzer 220 may be a computer system with added functionality provided by a conventional telemetry interface wand (not shown). Such wands include rf transmission and reception circuitry similar to that in the implantable cardiac arrhythmia alarm 5. The telemetry interface wand receives the signals sent by the implantable cardiac arrhythmia alarm 5. Software (not shown) in the external programmer and analyzer is configured to provide a human interface for controlling the operations performed by the cardiac arrhythmia alarm 5. In response to commands of the operator, the programmer and analyzer reads and displays data from the alarm 5, transmits control parameters to the alarm 5, and downloads diagnostic and application routine machine code from a program library into the RAM memory of the cardiac arrhythmia alarm 5.

The external programmer and analyzer 220 controls the implantable cardiac arrhythmia alarm 5 by sending control signals to it to direct its operations. The cardiac arrhythmia alarm 5 transmits application-specific data, for example heart motion signals to the external device for display and analysis. The external programmer and analyzer may use the data telemetered from the alarm 5 according to the specifications of a diagnostic or therapeutic protocol to determine what command to send to the alarm 5, and when to send it.

The personal communicator alarm 230 acts as the human interface between the implantable cardiac arrhythmia alarm 5 and the patient. The alarm responds to application-dependent messages from the alarm 5. Programs loaded from the external programmer and analyzer 220 into the alarm 5 include message output routines which are triggered by physiological or diagnostic events sensed by the alarm 5. Electronic components of the personal communicator alarm 230 are a subset of those comprising the external programmer and analyzer 220. These components, none of which are individually shown, may include a microprocessor, communication circuitry, and an acoustic or visual alarm signal for notifying the patient of triggering events. The telemetry receiver (not shown) within the personal communicator alarm 230 is similar to and compatible with that of the cardiac arrhythmia alarm 5. The cardiac arrhythmia alarm 5 sends message codes to the personal communicator alarm 230, causing it to respond by activating a light emitting diode or an acoustic alarm. In this manner the alarm 5 warns the patient to take medication or otherwise seek medical intervention.

In addition to its function as a warning device in response to alarm signals from the implantable cardiac arrhythmia alarm 5, the personal communicator alarm 230 may be used as a control device to activate certain control functions within the implantable cardiac arrhythmia alarm 5. For example, a physician wanting to view the electrical manifestation of a patient symptom may direct the patient to activate the personal communicator alarm 230 upon feeling the physical effects of the symptom. Similarly, the patient may set a timer in the personal communicator to activate telemetry at a particular time of day or night to allow analysis of physiological data sampled when the patient is in a particular state (sleeping, for example). The personal communicator alarm 230 may send a command to the implantable cardiac arrhythmia alarm 5 requesting the transmission of stored physiological event precursors or other signal information, including unprocessed signal samples. The cardiac arrhythmia alarm 5 may send the information to a third device such as the external programmer and analyzer 220, the telephonic communicator 240 or the full disclosure recorder 250.

The telephonic communicator 240 is another device for responding to messages from the implantable cardiac arrhythmia alarm 5. Programs loaded from the external programmer and analyzer 220 into the communicator 5 determine the physiological and diagnostic events to which the alarm 5 will respond by activating the telephonic communicator 240. The electronic components (not shown) of the telephonic communicator 240 are a subset of those comprising the external programer and analyzer 220 including a microprocessor and circuitry for receiving messages from the cardiac arrhythmia alarm 5 and for sending messages over telephone lines or a cellular telephone link. The telemetry receiver within the telephonic communicator 240 receives data in a manner similar to and compatible with that of the cardiac arrhythmia alarm 5. Event codes from the implantable unit cause the telephonic communicator 240 to establish a telephonic communication link with a previously designated physician or clinic. The telephonic communicator 240 accesses a telephone number according to the directions provided by either the alarm 5 or the programming within the telephonic communicator 240 itself. The telephonic communicator 240, like the cardiac arrhythmia alarm 5, is programmable by the external programmer and analyzer 220. Upon accessing the designated physician or clinic, the telephonic communicator 240 sends data and personal and diagnostic information supplied by the cardiac arrhythmia alarm 5.

Another optional component of the system is the full disclosure recorder 250, which allows visual inspection and analysis of the physiological signal recordings. In addition to a microprocessor and communication circuitry (not shown), the full disclosure recorder 250 may have additional memory for storing large amounts of data in the form of semiconductor RAM, magnetic disks, magnetic tapes, or any other mass storage memory means. The microprocessor may perform data compression and reduction routines to store data more efficiently.

From the foregoing discussion, it is apparent that the present invention provides a leadless implantable cardiac arrhythmia alarm capable of sensing impedance measurements of heart, respiratory and patient motion and, from these measurements, generating an alarm signal when the measurements indicate the occurrence of a cardiac arrhythmia. The alarm signal may be an acoustic warning or a telemetric communication to a non-implanted communication device. The invention accomplishes substantial improvements in providing a minimally invasive patient alarm which does not require the attachment of leads or the presence of feedthrough connectors to the hermetically sealed monitor. Furthermore, the alarm is provided with a capability of sensing multiple physiological parameters to automatically determine when a patient's heart is functioning in an abnormal manner.

Although the invention has been described with reference to particular embodiments, it is to be understood that such embodiments are merely illustrative of the application of the principles of the invention. Numerous modifications may be made therein and other arrangements may be devised without departing from the true spirit and scope of the invention.

We claim:

1. A cardiac arrhythmia alarm for chronic subcutaneous implantation within a patient's body, comprising:
    a hermetically-sealed housing;
    an electromagnetic sensor fully enclosed within said housing, said sensor including an antenna, means for applying measuring currents to said antenna, said measuring currents having frequency components within a range of from approximately 10 kilohertz to approximately 1000 megahertz, means for controlling said measuring current applying means to limit the frequency components of the applied measuring currents to lie within at least one predetermined subrange of frequencies such that the measured voltage within each subrange of frequencies corresponds to a measurement of physical motion within the patient's body relating to a particular physiological function, means for measuring voltages developed at said antenna in response to the application of said measuring currents, and means for deriving at least one physiological parameter from the measured voltage corresponding to each of said at least one predetermined subrange of frequencies;
    means responsive to said sensor for detecting a cardiac arrhythmia, said detecting means being fully enclosed within said housing; and
    said acoustic alarm within said housing responsive to said detecting means for notifying the patient of an arrhythmia condition.

2. A cardiac arrhythmia alarm in accordance with claim 1, wherein said measuring current applying means includes means for generating measuring currents in the form of short-duration, square-wave-like current pulses having pulse durations in the range from 5 nanoseconds to 20 microseconds, wherein said controlling means includes means for limiting said measuring current applying means to generate measuring current pulses having pulse durations within at least one predetermined subrange of durations, wherein said at least one derived physiological parameter is a heart motion parameter and its associated subrange of pulse durations includes durations longer than approximately 300 nanoseconds, and wherein said cardiac arrhythmia detecting means derives a heart rate measurement on the basis of said heart motion parameter and detects a physiological condition indicative of a cardiac arrhythmia when said heart rate measurement is greater than a predetermined abnormal heart rate.

3. A cardiac arrhythmia alarm in accordance with claim 2, wherein said physiological parameter deriving means derives a second physiological parameter, wherein said second physiological parameter is a respiration parameter and its associated subrange of pulse durations includes durations from approximately 25 nanoseconds to approximately 500 nanoseconds, wherein said cardiac arrhythmia detecting means derives a metabolic indicator rate on the basis of said respiration parameter and sets said predetermined abnormal heart rate as a function of said metabolic indicator rate.

4. A cardiac arrhythmia alarm in accordance with claim 1, wherein said measuring current applying means includes means for generating measuring currents in the form of sinusoidal-like oscillating currents having frequency components in the range from 10 kilohertz to 1000 megahertz, wherein said controlling means includes means for limiting said measuring current applying means to generate measuring currents having sinusoidal-like oscillating frequencies within at least one predetermined subrange of frequencies, wherein said at least one derived physiological parameter is a heart motion parameter and its associated subrange of oscillating current frequencies includes frequencies lower than approximately 4 megahertz, and wherein said cardiac arrhythmia detecting means derives a heart rate measurement on the basis of said heart motion parameter and detects a physiological condition indicative of a cardiac arrhythmia when said heart rate measurement is greater than a predetermined abnormal heart rate.

5. A cardiac arrhythmia alarm in accordance with claim 4, wherein said physiological parameter deriving means derives a second physiological parameter, wherein said second physiological parameter is a respiration parameter and its associated subrange of oscillating current frequencies includes frequencies from approximately 2 megahertz to approximately 40 megahertz, wherein said cardiac arrhythmia detecting means derives a metabolic indicator rate on the basis of said respiration parameter and sets said predetermined abnormal heart rate as a function of said metabolic indicator rate.

6. A cardiac arrhythmia alarm for chronic subcutaneous implantation within a patient's body, capable of communicating with an information-receiving device, comprising:

a hermetically-sealed housing;

an electromagnetic sensor fully enclosed within said housing, said sensor including an antenna, means for applying measuring currents to said antenna, said measuring currents having frequency components within a range of from approximately 10 kilohertz to approximately 1000 megahertz, means for controlling said measuring current applying means to limit the frequency components of the applied measuring currents to lie within at least one predetermined subrange of frequencies such that the measured voltage within each subrange of frequencies corresponds to a measurement of physical motion within the patient's body relating to a particular physiological function, means for measuring voltages developed at said antenna in response to the application of said measuring currents, and means for deriving at least one physiological parameter from the measured voltage corresponding to each of said at least one predetermined subrange of frequencies;

means responsive to said sensor for determining a heart abnormality, said detecting means being fully enclosed within said housing; and a transmitter within said housing responsive to said determining means for communicating with said information-receiving device to report on the heart abnormality.

7. A cardiac arrhythmia alarm in accordance with claim 6, wherein said transmitter includes means to initiate a communication with said information-receiving device independent of the operation of said information-receiving device.

8. A cardiac arrhythmia alarm in accordance with claim 7, wherein said transmitter includes means to report a heart abnormality in the form of a diagnostic message.

9. A cardiac arrhythmia alarm in accordance with claim 6, wherein said sensor, said determining means and said transmitter all include means to operate continuously, independently of external control by said information-receiving device.

10. A cardiac arrhythmia alarm in accordance with claim 6, wherein said measuring current applying means includes a circuit to generate a constant measuring current.

11. A cardiac arrhythmia alarm in accordance with claim 6, wherein said measuring current applying means includes a circuit to generate measuring current using a constant voltage.

12. A cardiac arrhythmia alarm in accordance with claim 6, wherein said measuring current applying means includes means for generating measuring currents in the form of short-duration, square-wave-like current pulses having pulse durations in the range from 5 nanoseconds to 20 microseconds, wherein said controlling means includes means for limiting said measuring current applying means to generate measuring current pulses having pulse durations within at least one predetermined subrange of durations, wherein said at least one derived physiological parameter is a heart motion parameter and its associated subrange of pulse durations includes durations longer than approximately 300 nanoseconds, and wherein said heart abnormality determining means derives a heart rate measurement on the basis of said heart motion parameter and detects a physiological condition indicative of a heart abnormality when said heart rate measurement is greater than a predetermined abnormal heart rate.

13. A cardiac arrhythmia alarm in accordance with claim 12, wherein said physiological parameter deriving means derives a second physiological parameter, wherein said second physiological parameter is a respiration parameter and its associated subrange of pulse durations includes durations from approximately 25 nanoseconds to approximately 500 nanoseconds, and wherein said heart abnormality determining means derives a metabolic indicator rate on the basis of said respiration parameter and sets said predetermined abnormal heart rate as a function of said metabolic indicator rate.

14. A cardiac arrhythmia alarm in accordance with claim 6, wherein said measuring current applying means includes means for generating measuring currents in the form of short-duration, square-wave-like current pulses, wherein said controlling means includes means for regulating said measuring current applying means to generate measuring current pulses having a predetermined pulse duration, said regulating means regulating, for each of said measuring current pulses, at least one subrange of sampling times with respect to the onset of the current pulse at which said measuring current applying means measures the voltage developed at said antenna by the current pulse, and wherein said at least one subrange of sampling times defines a sampling frequency which corresponds to a measurement of a physiological parameter.

15. A cardiac arrhythmia alarm in accordance with claim 14, wherein said at least one derived physiological parameter is a heart motion parameter and its associated subrange of sampling times includes times longer than approximately 300 nanoseconds, and wherein said heart abnormality determining means derives a heart rate measurement on the basis of said heart motion parameter and detects a physiological condition indicative of a heart abnormality when the heart rate parameter is greater that a predetermined abnormal heart rate.

16. A cardiac arrhythmia alarm in accordance with claim 15, wherein said physiological parameter deriving means derives a second physiological parameter, wherein said second physiological parameter is a respiration parameter and its associated subrange of sampling times includes times from approximately 25 nanoseconds to approximately 500 nanoseconds, and wherein said heart abnormality determining means derives a metabolic indicator rate on the basis of said respiration parameter and sets the predetermined abnormal heart rate as a function of said metabolic indicator rate.

17. A cardiac arrhythmia alarm in accordance with claim 6, wherein said measuring current applying means includes means for generating measuring currents in the form of sinusoidal-like oscillating currents having frequency components in the range from 10 kilohertz to 1000 megahertz, wherein said controlling means includes means for limiting said measuring current applying means to generate measuring currents having sinusoidal-like oscillating frequencies within at least one predetermined subrange of frequencies, wherein said at least one derived physiological parameter is a heart motion parameter and its associated subrange of oscillating current frequencies includes frequencies lower than approximately 4 megahertz, and wherein said heart abnormality determining means derives a heart rate measurement on the basis of said heart motion parameter and detects a physiological condition indicative of a heart abnormality when said heart rate measurement is greater that a predetermined abnormal heart rate.

18. A cardiac arrhythmia alarm in accordance with claim 17, wherein said physiological parameter deriving means derives a second physiological parameter, wherein said second physiological parameter is a respiration parameter and its associated subrange of oscillating current frequencies includes frequencies from approximately 2 megahertz to approximately 40 megahertz, and wherein said heart abnormality determining means derives a metabolic indicator rate on the basis of said respiration parameter and sets said predetermined abnormal heart rate as a function of said metabolic indicator rate.

19. A cardiac arrhythmia alarm in accordance with claim 6, wherein said measuring current applying means includes means for generating measuring currents in the form of timed pulses of sinusoidal-like oscillating currents having timed pulses of durations of at least 5 nanoseconds and having frequency components in the range of from 10 kilohertz to 1000 megahertz, and wherein said controlling means includes means for limiting said measuring current applying means to generate measuring currents having oscillating frequencies within at least one predetermined subrange of frequencies.

20. A cardiac arrhythmia alarm for chronic subcutaneous implantation within a patient's body, capable of communicating with an information-receiving device, comprising:
a hermetically-sealed housing;
an electromagnetic sensor fully enclosed within said housing, said sensor including an antenna, means for applying measuring currents to said antenna, said measuring currents having frequency components within a range of from approximately 10 kilohertz to approximately 1000 megahertz, means for controlling said measuring current applying means to limit the frequency components of the applied measuring currents to lie within at least one predetermined subrange of frequencies such that the measured voltage within each subrange of frequencies corresponds to a measurement of physical motion within the patient's body relating to a particular physiological function, means for measuring voltages developed at said antenna in response to the application of said measuring currents, and means for deriving at least one physiological parameter from the measured voltage corresponding to each of said at least one predetermined subrange of frequencies;
means responsive to said sensor for deriving cardiac information therefrom, said responsive means being fully enclosed within said housing; and
means within said housing responsive to said deriving means for communicating with said information-receiving device to report on the derived cardiac information.

21. A method for monitoring a patient's heartbeat signals using a hermetically-sealed cardiac arrhythmia alarm apparatus to detect and warn of a cardiac arrhythmia condition comprising the steps of:
measuring impedance within the patient's body, said impedance measuring step comprising the substeps of applying measuring currents to an antenna fully enclosed within the apparatus and measuring voltages developed at the antenna in response to the application of said measuring currents, said measuring currents having frequency components within a range from approximately 10 kilohertz to approximately 1000 megahertz;
controlling the frequency components of the applied measuring current to lie within at least one predetermined subrange of frequencies such that the measured voltage within each subrange of frequencies corresponds to a measurement of a physiological parameter;
deriving at least one physiological parameter from the measured voltage corresponding to each of said at least one predetermined subrange of frequencies;
analyzing the derived at least one physiological parameter to detect a physiological condition indicative of a heart abnormality; and
upon the detection of a heart abnormality, activating an acoustic alarm within said apparatus to notify the patient of said heart abnormality.

22. A method in accordance with claim 21, wherein said impedance measuring step includes the further substep of generating said measuring currents in the form of short-duration, square-wave-like current pulses having pulse durations in the range of from 5 nanoseconds to 20 microseconds, and wherein said controlling step includes the substep of regulating said impedance measuring step to generate measuring current pulses having pulse durations within at least one predetermined subrange of durations.

23. A method in accordance with claim 22, wherein said controlling step includes the substep of regulating said impedance measuring step to generate measuring current pulses having pulse durations longer than approximately 300 nanoseconds.

24. A method in accordance with claim 23, wherein said at least one derived physiological parameter is a heart motion parameter, and wherein said analyzing step includes the substeps of determining a heart rate parameter on the basis of said heart motion parameter and detecting a physiological condition indicative of a heart abnormality when said heart rate parameter is greater than a predetermined abnormal heart rate.

25. A method in accordance with claim 24, wherein said deriving step includes the substep of driving a second physiological parameter, said second physiological parameter being a respiration parameter, and wherein said controlling step includes the further substep of regulating said impedance measuring step to also generate measuring current pulses having pulse durations from approximately 25 nanoseconds to approximately 500 nanoseconds.

26. A method in accordance with claim 25, wherein said analyzing step includes the further substeps of deriving a metabolic indicator rate on the basis of said respiration parameter and setting said predetermined abnormal heart rate as a function of said metabolic indicator rate.

27. A method in accordance with claim 24, wherein said deriving step includes the substep of deriving a second physiological parameter, said second physiological parameter being a patient motion parameter, and wherein said controlling step includes the further substep of regulating said impedance measuring step to also generate measuring current pulses having pulse durations shorter than approximately 125 nanoseconds.

28. A method in accordance with claim 27, wherein said analyzing step includes the further substeps of deriving a metabolic indicator rate on the basis of said patient motion parameter and setting said predetermined abnormal heart rate as a function of said metabolic indicator rate.

29. A method in accordance with claim 21, wherein said impedance measuring step includes the further substep of generating said measuring currents in the form of oscillating measuring currents having frequency components in the range of from 10 kilohertz to 1000 megahertz, and wherein said controlling step includes the substep of limiting said impedance measuring step to generating measuring currents having oscillating current frequencies.

30. A method in accordance with claim 29, wherein said controlling step includes the substep of regulating said impedance measuring step to generate oscillating measuring currents having frequencies lower than approximately 4 megahertz.

31. A method in accordance with claim 30, wherein said at least one derived physiological parameter is a heart motion parameter, and wherein said analyzing step includes the substeps of determining a heart rate parameter on the basis of said heart motion parameter and detecting a physiological condition indicative of a heart abnormality when said heart rate parameter is greater than a predetermined abnormal heart rate.

32. A method in accordance with claim 31, wherein said deriving step includes the substep of deriving a second physiological parameter, said second physiological parameter being a respiration parameter, and wherein said controlling step includes the further substep of regulating said impedance measuring step to also generate oscillating measuring currents having frequencies from approximately 2 megahertz to approximately 40 megahertz.

33. A method in accordance with claim 32, wherein said analyzing step includes the further substeps of deriving a metabolic indicator rate on the basis of said respiration parameter and setting said predetermined abnormal heart rate as a function of said metabolic indicator rate.

34. A method in accordance with claim 31, wherein said deriving step includes the substep of deriving a second physiological parameter, said second physiological parameter being a patient motion parameter, and wherein said controlling step includes the further substep of regulating said impedance measuring step to also generate oscillating measuring currents having frequencies higher than approximately 8 megahertz.

35. A method in accordance with claim 34, wherein said analyzing step includes the further substeps of deriving a metabolic indicator rate on the basis of said patient motion parameter and setting said predetermined abnormal heart rate as a function of said metabolic indicator rate.

36. A method in accordance with claim 21, wherein said impedance measuring step includes the further substep of generating measuring currents in the form of timed pulses of sinusoidal-like oscillating currents having timed pulses of durations of at least 5 nanoseconds and having frequency components in the range from 10 kilohertz to 1000 megahertz, wherein said controlling step includes the substep of limiting said impedance measuring step to generate measuring currents having oscillating current frequencies within at least one predetermined subrange of frequencies, and wherein the measured voltage within each subrange of frequencies corresponds to a measurement of a physiological parameter.

37. A method in accordance with claim 21, further comprising the steps of:
upon the detection of a heart abnormality, initiating communication with a non-implanted message-receiving device independent of the operation of said message-receiving device; and
transmitting diagnostic messages to said message-receiving device upon initiation of communication.

38. A leadless cardiac sensor assembly for chronic subcutaneous implantation within a patient's body, comprising:
a hermetically-sealed housing; and
an electromagnetic sensor fully enclosed within said housing, said sensor including an antenna, means for applying excitation signals to said antenna, said excitation signals having frequency components within a range of from approximately 10 kilohertz to approximately 1000 megahertz, means for controlling said excitation signal applying means to limit the frequency components of the applied excitation signals to lie within at least one predetermined subrange of frequencies such that a received signal within each subrange of frequencies corresponds to a measurement of physical motion within the patient's body relating to a particular physiological function, means for measuring received signals developed at said antenna in response to the application of said excitation signals, and means for deriving at least one physiological parameter from the received signal corresponding to each of said at least one predetermined subrange of frequencies.

39. The leadless sensor in accordance with claim 38, wherein said excitation signal applying means includes means for generating excitation signals in the form of short-duration, square-wave-like signal pulses having pulse durations in the range from 5 nanoseconds to 20 microseconds, wherein said controlling means includes means for limiting said excitation signal applying means to generate excitation signals having pulse durations within at least one predetermined subrange of durations, and wherein said at least one derived physiological parameter is a heart motion parameter.

40. The leadless sensor in accordance with claim 39, wherein said physiological parameter deriving means derives a second physiological parameter, wherein said second physiological parameter is a respiration parameter and its associated subrange of pulse durations includes durations from approximately 25 nanoseconds to approximately 500 nanoseconds, said sensor further comprising heart rate means for deriving a heart rate on the basis of said respiration parameter.

41. A device for monitoring body organs, body tissues or fluid contents thereof, said device comprising:
 a hermetically-sealed housing; and
 an electromagnetic sensor fully enclosed within said housing, said sensor including:
 (a) an antenna,
 (b) means for applying excitation signals to said antenna, said excitation signals having frequency components exceeding 10 kilohertz,
 (c) means for controlling said excitation signal applying means to limit the frequency components of the applied excitation signals to lie within at least one predetermined subrange of frequencies such that a received signal within each subrange of frequencies corresponds to a physiological parameter within the patient's body relating to a particular physiological function,
 (d) means for measuring received signals developed at said antenna in response to the application of said excitation signals, and
 (e) means for deriving said parameter from the received signals.

42. The device of claim 41 wherein said physical parameter relates to the motion of said patient's heart.

43. The device of claim 41 wherein said physical parameter relates to a tissue motion within said patient.

44. A method for monitoring a patient's heartbeat signals using a hermetically-sealed leaderless sensor apparatus to generate a signal indicative of a cardiac parameter comprising the steps of:
 measuring impedance within the patient's body, said impedance measuring step comprising the substeps of applying measuring currents to an antenna fully enclosed within the apparatus and measuring signals developed at the antenna in response to the application of said measuring currents, said measuring currents having frequency components within a range from approximately 10 kilohertz;
 controlling the frequency components of the applied measuring current to lie within at least one predetermined subrange of frequencies such that the measured signal within each subrange of frequencies corresponds to a measurement of a physiological parameter; and
 deriving at least one physiological parameter from the measured voltage corresponding to said at least one predetermined subrange of frequencies.

* * * * *